US010188282B2

(12) United States Patent
Takii et al.

(10) Patent No.: US 10,188,282 B2
(45) Date of Patent: Jan. 29, 2019

(54) SUBJECTIVE OPTOMETRY APPARATUS

(71) Applicant: NIDEK CO., LTD., Aichi (JP)

(72) Inventors: Michihiro Takii, Aichi (JP); Masaaki Hanebuchi, Aichi (JP); Hisashi Ochi, Aichi (JP)

(73) Assignee: NIDEK CO., LTD., Aichi (JP)

( * ) Notice: Subject to any disclaimer, the term of this patent is extended or adjusted under 35 U.S.C. 154(b) by 195 days.

(21) Appl. No.: 15/347,915

(22) Filed: Nov. 10, 2016

(65) Prior Publication Data

US 2017/0135572 A1 May 18, 2017

(30) Foreign Application Priority Data

Nov. 13, 2015 (JP) ................................ 2015-222931
Nov. 13, 2015 (JP) ................................ 2015-222932
Nov. 13, 2015 (JP) ................................ 2015-222933

(51) Int. Cl.

*A61B 3/032* (2006.01)
*A61B 3/00* (2006.01)
*A61B 3/04* (2006.01)
*A61B 3/103* (2006.01)
*A61B 3/18* (2006.01)

(Continued)

(52) U.S. Cl.

CPC ............ *A61B 3/032* (2013.01); *A61B 3/0008* (2013.01); *A61B 3/0025* (2013.01); *A61B 3/0041* (2013.01); *A61B 3/0075* (2013.01); *A61B 3/02* (2013.01); *A61B 3/028* (2013.01); *A61B 3/04* (2013.01); *A61B 3/10* (2013.01); *A61B 3/103* (2013.01); *A61B 3/18* (2013.01); *G02B 27/0068* (2013.01)

(58) Field of Classification Search

CPC ....... A61B 3/0032; A61B 3/18; A61B 3/0008; A61B 3/0075; A61B 3/103; A61B 3/0041; A61B 3/0025; A61B 3/04; G02B 27/0068

See application file for complete search history.

(56) References Cited

U.S. PATENT DOCUMENTS 3,874,774 A 4/1975 Humphrey
4,465,348 A 8/1984 Blaha (Continued)

FOREIGN PATENT DOCUMENTS

JP 05-176893 7/1993
JP 06-46999 2/1994
JP 08224214 9/1996

OTHER PUBLICATIONS

Partial European Search Report dated May 11, 2017 for the corresponding European Patent Application No. 16197991.9.

*Primary Examiner* — Jack Dinh
(74) *Attorney, Agent, or Firm* — Rankin, Hill & Clark LLP

(57) ABSTRACT

A subjective optometry apparatus includes: a subjective measurer including a light projecting optical system, a corrective optical system including a right-eye corrective optical system and a left-eye corrective optical system, and an optical member for guiding the target light flux corrected by the corrective optical system to an examinee's eye, the subjective measurer subjectively measuring an optical characteristic of the examinee's eye; and an objective measurer including a measurement optical system for emitting measurement light to a fundus of the examinee's eye and for receiving reflected light from the fundus, the objective measurer objectively measuring the optical characteristic of the examinee's eye via the optical member disposed on an optical path of the measurement optical system.

14 Claims, 8 Drawing Sheets

(51) Int. Cl.

| | |
|---|---|
| ***G02B 27/00*** | (2006.01) |
| ***A61B 3/02*** | (2006.01) |
| ***A61B 3/028*** | (2006.01) |
| ***A61B 3/10*** | (2006.01) |

(56) References Cited

U.S. PATENT DOCUMENTS

| | | | |
|---|---|---|---|
| 5,463,430 | A | 10/1995 | Isogai et al. |
| 5,483,305 | A | 1/1996 | Kohayakawa |
| 2005/0280777 | A1 | 12/2005 | Dai |
| 2012/0162606 | A1 | 6/2012 | Nakamura |
| 2014/0211165 | A1 | 7/2014 | Hosoi |

SUBJECTIVE OPTOMETRY APPARATUS

CROSS-REFERENCE TO RELATED APPLICATION

This application claims priority from Japanese Patent Application Nos. 2015-222931, 2015-222932, and 2015-222933 filed with the Japan Patent Office on Nov. 13, 2015, the entire contents of which are hereby incorporated by reference.

BACKGROUND

1. Technical Field

The present disclosure relates to a subjective optometry apparatus.

2. Description of the Related Art

A subjective optometry apparatus subjectively measures optical characteristics of an examinee's eye, for example. In a subjective optometry apparatus disclosed in JP-A-5-176893, for example, a corrective optical system with adjustable refractivity is placed in front of the examinee's eyes each individually. By projection of light via the corrective optical system, an image of an examination target is formed on the fundus of the examinee's eye. The examiner determines a corrective value by adjusting the corrective optical system in accordance with a response from the examinee, until the examinee can properly see the target. Based on the corrective value, the examiner measures the refractive power of the examinee's eye. In another example, a subjective optometry apparatus disclosed in U.S. Pat. No. 3,874,774, an image of an examination target is formed in front of the examinee's eye via a corrective optical system. In this apparatus, the refractive power of the examinee's eye is measured without placing the corrective optical system in front of the eye.

SUMMARY

A subjective optometry apparatus includes: a subjective measurer including a light projecting optical system for projecting a target light flux toward an examinee's eye, a corrective optical system including a right-left pair of a right-eye corrective optical system and a left-eye corrective optical system and disposed on an optical path of the light projecting optical system to modify an optical characteristic of the target light flux, and an optical member shared by a right-eye optical path including the right-eye corrective optical system and a left-eye optical path including the left-eye corrective optical system, the optical member for guiding the target light flux corrected by the corrective optical system to the examinee's eye, the subjective measurer subjectively measuring an optical characteristic of the examinee's eye; and an objective measurer including a measurement optical system for emitting measurement light to a fundus of the examinee's eye and for receiving reflected light from the fundus, the objective measurer objectively measuring the optical characteristic of the examinee's eye via the optical member disposed on an optical path of the measurement optical system.

DESCRIPTION OF THE EMBODIMENTS

Figure 1:
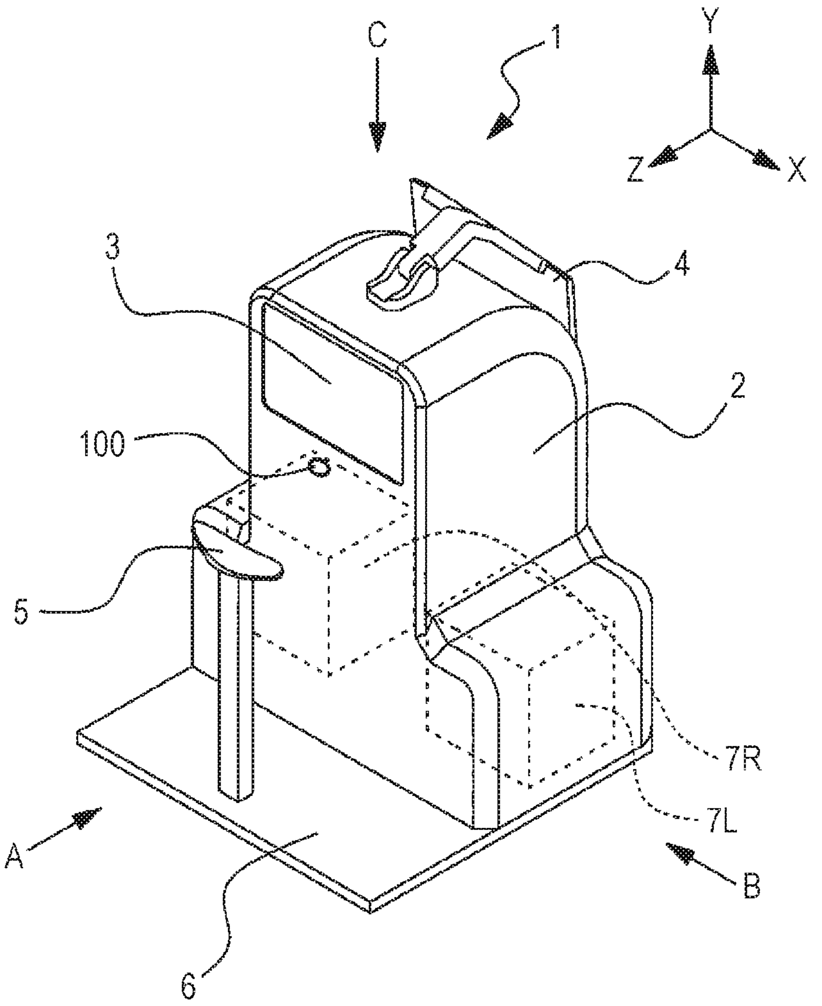
FIG. 1 is an external view of a subjective optometry apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

When the optical characteristics of the examinee's eye are measured, if an apparatus is used of which a part is disposed in front of the eye, the examinee's eye may react with accommodation with respect to the part of the apparatus placed in front of the eye, resulting in a decrease in measurement accuracy. Accordingly, when measuring the optical characteristics of the examinee's eye, it is preferable to measure the optical characteristics by subjective measurement and objective measurement in a natural state as if the examinee were seeing an object in daily life (an open state in which a part of the apparatus is not placed in front of the eye).

An object of the present disclosure is to provide a subjective optometry apparatus as follows. The subjective optometry apparatus enables subjective measurement and objective measurement in a natural state, and is adapted to perform accurate measurement.

In typical subjective optometry apparatuses, optical aberration may be caused by various members of the apparatus, and the optical aberration is corrected. However, the optical aberration may vary depending on measurement conditions (such as eye refractive power, examination distance, and convergence angle) during the subjective measurement of the optical characteristics of the examinee's eye. Accordingly, if the correction is performed with a certain correction amount for correcting the optical aberration, it may become difficult to suppress the optical aberration.

Another object of the present disclosure is to provide a subjective optometry apparatus as follows. The subjective optometry apparatus is adapted to suppress optical aberration and accurately measure the optical characteristics of an examinee's eye.

In the subjective optometry apparatus, when the optical characteristics of the examinee's eye are subjectively measured, an operation for adjusting the positional relationship between the examinee's eye and the subjective optometry apparatus (alignment operation) is important. If the alignment operation is not properly performed during the subjective measurement of the optical characteristics of the examinee's eye, the accuracy of the result of measurement of the optical characteristics of the examinee's eye may be decreased, for example. In addition, the adjustment of the positional relationship between the examinee's eye and the subjective optometry apparatus may take time. In this case, the alignment operation may fail to be performed efficiently when subjectively measuring the optical characteristics of the examinee's eye.

Yet another object of the present disclosure is to provide a subjective optometry apparatus as follows. The subjective optometry apparatus is adapted to measure the optical characteristics of the examinee's eye accurately during subjective measurement of the optical characteristics of the examinee's eye. The subjective optometry apparatus is also adapted to perform the alignment operation efficiently.

A subjective optometry apparatus according to a first aspect of the present disclosure includes: a subjective measurer including a light projecting optical system for projecting a target light flux toward an examinee's eye, a corrective optical system including a right-left pair of a right-eye corrective optical system and a left-eye corrective optical system and disposed on an optical path of the light projecting optical system to modify an optical characteristic of the target light flux, and an optical member shared by a right-eye optical path including the right-eye corrective optical system and a left-eye optical path including the left-eye corrective optical system, the optical member for guiding the target light flux corrected by the corrective optical system to the examinee's eye, the subjective measurer subjectively measuring an optical characteristic of the examinee's eye; and an objective measurer including a measurement optical system for emitting measurement light to a fundus of the examinee's eye and for receiving reflected light from the fundus, the objective measurer objectively measuring the optical characteristic of the examinee's eye via the optical member disposed on an optical path of the measurement optical system.

For the subjective optometry apparatus according to a second aspect of the present disclosure, an optical axis between the optical member and the examinee's eye in the subjective measurer, and an optical axis between the optical member and the examinee's eye in the objective measurer are coaxial, in the subjective optometry apparatus according to the first aspect of the present disclosure.

For the subjective optometry apparatus according to a third aspect of the present disclosure, the optical member includes a concave mirror; and the subjective measurer guides the target light flux to the examinee's eye by reflecting, using the concave mirror, the target light flux corrected by the corrective optical system toward the examinee's eye, and guides an image of the target light flux corrected by the corrective optical system to the examinee's eye in such a way that a distance between a formation position of the image and the examinee's eye as sensed by the examinee becomes an optically predetermined examination distance, in the subjective optometry apparatus according to the first aspect of the present disclosure.

The subjective optometry apparatus according to a fourth aspect of the present disclosure further includes in the subjective optometry apparatus according to the first aspect of the present disclosure: a displacement detector for detecting displacement of an image of the corrective optical system with respect to the examinee's eye; a right-left pair of deflecting members disposed between the corrective optical system and the examinee's eye; a driver for driving the deflecting members; and a corrector for optically correcting a formation position of the image by deflecting an apparent light flux for guiding the image of the corrective optical system to the examinee's eye, by controlling the driver based on a result of detection by the displacement detector.

The subjective optometry apparatus according to a fifth aspect of the present disclosure further includes in the subjective optometry apparatus according to the first aspect of the present disclosure: a correction setter for setting a correction amount for correcting optical aberration caused in the subjective measurer, based on a corrective power of the corrective optical system; and an aberration corrector for correcting the optical aberration caused in the subjective measurer based on the correction amount set by the correction setter.

The subjective optometry apparatus according to a sixth aspect of the present disclosure further includes in the subjective optometry apparatus according to the first aspect of the present disclosure: a controller for modifying a presentation distance of a target by the target light flux by modifying a formation position of an image of the target light flux; a correction setter for setting a correction amount for correcting optical aberration caused in the subjective measurer, based on the presentation distance; and an aberration corrector for correcting the optical aberration caused in the subjective measurer based on the correction amount set by the correction setter.

The subjective optometry apparatus according to a seventh aspect of the present disclosure further includes in the subjective optometry apparatus according to the first aspect of the present disclosure: a convergence angle modifier for modifying a convergence angle of the target light flux emitted from the right-eye optical path and the left-eye optical path; a correction setter for setting a correction amount for correcting optical aberration caused in the subjective measurer, based on the convergence angle; and an aberration corrector for correcting the optical aberration caused in the subjective measurer based on the correction amount set by the correction setter.

For the subjective optometry apparatus according to an eighth aspect of the present disclosure, the aberration corrector corrects the optical aberration using the corrective optical system, in the subjective optometry apparatus according to the fifth aspect of the present disclosure.

The subjective optometry apparatus according to a ninth aspect of the present disclosure further includes in the subjective optometry apparatus according to the fifth aspect of the present disclosure an insertion/removal unit for controlling insertion and removal of an auxiliary optical member on an optical path of the subjective measurer.

The subjective optometry apparatus according to a tenth aspect of the present disclosure further includes in the subjective optometry apparatus according to the ninth aspect of the present disclosure a determiner for determining whether the auxiliary optical member is required or not, based on an eye refractive power acquired by the objective measurer. The insertion/removal unit controls insertion and removal of the auxiliary optical member on the optical path of the subjective measurer, based on a result of determination by the determiner.

The subjective optometry apparatus according to an eleventh aspect of the present disclosure further includes in the subjective optometry apparatus according to the fifth aspect of the present disclosure: a determiner for determining whether an auxiliary optical member is required or not based on an eye refractive power acquired by the objective measurer; and a display unit for displaying, on a monitor, notification information based on a result of determination by the determiner.

The subjective optometry apparatus according to a twelfth aspect of the present disclosure further includes in the subjective optometry apparatus according to the first aspect of the present disclosure: an acquisitor for acquiring an objectively measured eye refractive power of the examinee's eye; and a setter for setting an alignment allowable range for determining an alignment state between the examinee's eye and the subjective measurer, based on the eye refractive power.

For the subjective optometry apparatus according to a thirteenth aspect of the present disclosure, the setter sets the alignment allowable range to be smaller as a diopter value increases in a plus direction or minus direction from zero diopter with reference to the zero diopter, in the subjective optometry apparatus according to the twelfth aspect of the present disclosure.

For the subjective optometry apparatus according to a fourteenth aspect of the present disclosure, the acquisitor acquires the eye refractive power of examinee's eye based on a result of measurement by the objective measurer, in the subjective optometry apparatus according to the twelfth aspect of the present disclosure.

A subjective optometry apparatus according to a fifteenth aspect of the present disclosure includes: a subjective measurer including a light projecting optical system for projecting a target light flux toward an examinee's eye, a corrective optical system disposed on an optical path of the light projecting optical system to modify an optical characteristic of the target light flux, and an optical member for guiding the target light flux corrected by the corrective optical system to the examinee's eye, the subjective measurer subjectively measuring an optical characteristic of the examinee's eye; a correction setter for setting a correction amount for correcting optical aberration caused in the subjective measurer, based on a corrective power of the corrective optical system; and an aberration corrector for correcting the optical aberration caused in the subjective measurer, based on the correction amount set by the correction setter.

The subjective optometry apparatus according to a sixteenth aspect of the present disclosure further includes in the subjective optometry apparatus according to the fifteenth aspect of the present disclosure an insertion/removal unit for controlling insertion and removal of an auxiliary optical member on an optical path of the subjective measurer.

The subjective optometry apparatus according to seventeenth aspect of the present disclosure further includes a determiner for determining whether the auxiliary optical member is required or not based on an eye refractive power acquired by the objective measurer in the subjective optometry apparatus according to the sixteenth aspect of the present disclosure. The insertion/removal unit controls the insertion and removal of the auxiliary optical member on the optical path of the subjective measurer based on a result of determination by the determiner.

The subjective optometry apparatus according to an eighteenth aspect of the present disclosure further includes in the subjective optometry apparatus according to the fifteenth aspect of the present disclosure: a determiner for determining whether the auxiliary optical member is required or not based on an eye refractive power acquired by an objective measurer; and a display unit for displaying, on a monitor, notification information based on a result of determination by the determiner.

A subjective optometry apparatus according to a nineteenth aspect of the present disclosure includes: a subjective measurer including a light projecting optical system for projecting a target light flux toward an examinee's eye, and a corrective optical system disposed on an optical path of the light projecting optical system to modify an optical characteristic of the target light flux, the subjective measurer subjectively measuring an optical characteristic of the examinee's eye; an acquisitor for acquiring an objectively measured eye refractive power of the examinee's eye; and a setter for setting an alignment allowable range for determining an alignment state between the examinee's eye and the subjective measurer, based on the eye refractive power.

For the subjective optometry apparatus according to a twentieth aspect of the present disclosure, the setter sets the alignment allowable range to be smaller as a diopter value increases in a plus direction or minus direction from zero diopter with reference to the zero diopter, in the subjective optometry apparatus according to the nineteenth aspect of the present disclosure.

In the following, a typical embodiment will be described with reference to the drawings. In the following descriptions, the depth direction of a subjective optometry apparatus 1 (front-rear direction with respect to the examinee during measurement of the examinee) will be referred to as a Z-direction. The horizontal direction in a plane perpendicular to the depth direction (right-left direction with respect to the examinee during measurement of the examinee) will be referred to as an X-direction. The vertical direction (up-down direction with respect to the examinee during measurement of the examinee) will be referred to as a Y-direction. In the following, suffixes "R" and "L" to reference signs respectively indicate uses for the right eye and the left eye.

FIG. 1 is an external view of the subjective optometry apparatus 1 according to the present embodiment. The subjective optometry apparatus 1 according to the present embodiment is provided with a housing 2, a presentation window 3, an operating unit (monitor) 4, a chin rest 5, a base 6, and an imaging optical system 100, for example. The housing 2 accommodates members therein, for example. For example, the housing 2 is internally provided with a right-eye measurer 7R and a left-eye measurer 7L (the portions indicated by broken lines in FIG. 1; the details will be described later). In the following, the right-eye measurer 7R and the left-eye measurer 7L may be collectively referred to as a measurer 7 when they are not distinguished. In the present embodiment, the right-eye measurer 7R and the left-eye measurer 7L are provided with identical members. That is, the subjective optometry apparatus 1 includes a right-left pair of subjective measurers and a right-left pair of objective measurers. The right-eye measurer 7R and the left-eye measurer 7L may, of course, be configured to be different with respect to at least some of the members.

The presentation window 3 is used for presenting a target to the examinee, for example. For example, target light fluxes from the right-eye measurer 7R and the left-eye measurer 7L are respectively projected onto the right eye ER and the left eye EL (see FIG. 3) of the examinee via the presentation window 3. In the following, the right eye ER and the left eye EL may be collectively referred to as the examinee's eye E when it is not necessary to distinguish the two.

The monitor (display) 4 is a touch panel, for example. Specifically, in the present embodiment, the monitor 4 functions as an operating unit. The monitor 4 outputs signals corresponding to input operation instructions to a calculation controller 70, which will be described later. The monitor 4 and the operating unit may of course be provided as separate members. The operating unit may include at least any one of operation units among a mouse, a joystick, and a keyboard.

The monitor 4 may be a display mounted to the body of the subjective optometry apparatus 1, or a display connected to the body of the subjective optometry apparatus 1, for example. Obviously, the monitor 4 may not be of touch panel type. The monitor 4 may be provided by the display of a personal computer (hereafter referred to as "PC"). The monitor 4 may be provided by a plurality of displays used in combination. The monitor 4 displays measurement results, for example.

The chin rest 5 is used for suppressing large tremors of the face, for example, so as to maintain a constant distance between the examinee's eye E and the subjective optometry apparatus 1. The chin rest 5 and the housing 2 are fixed to the base 6. In the present embodiment, the chin rest 5 is used to maintain a constant distance between the examinee's eye E and the subjective optometry apparatus 1. However, the configuration for maintaining a constant distance between the examinee's eye E and the subjective optometry apparatus 1 is not limited to the chin rest 5. Other examples of the configuration for maintaining a constant distance between the examinee's eye E and the subjective optometry apparatus 1 include a forehead rest and a face rest.

The imaging optical system 100 includes an imaging device and lenses, for example, which are not illustrated. The imaging optical system 100 is used to photograph the examinee's face, for example.

<Measurer>

Figure 2:
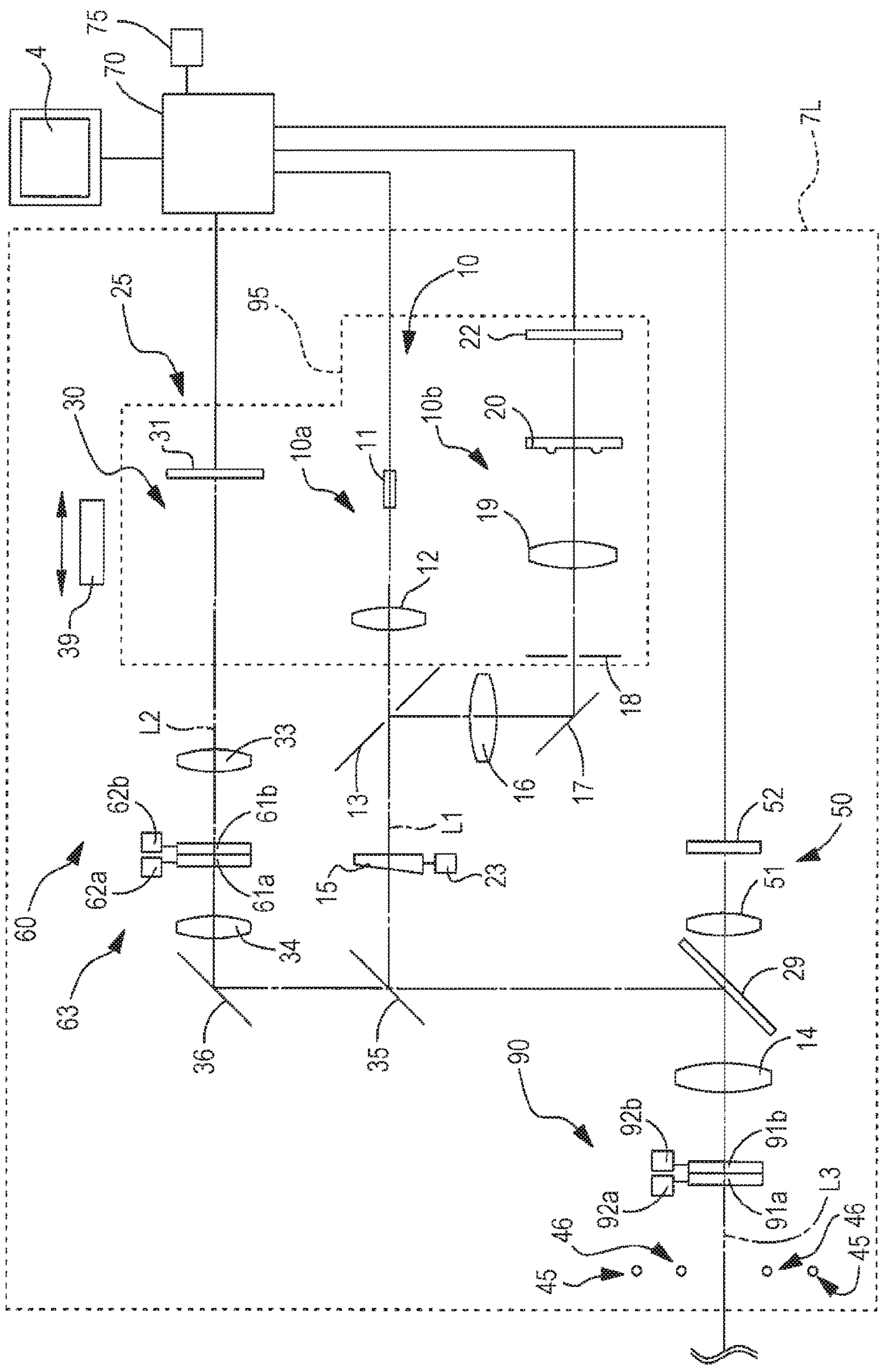
FIG. 2 is a drawing for describing a configuration of a measurer.

FIG. 2 is a drawing for describing the configuration of the measurer 7. In the present embodiment, the left-eye measurer 7L will be described by way of example. Description of the right-eye measurer 7R is omitted because it has the same configuration as that of the left-eye measurer 7L. The left-eye measurer 7L is provided with a subjective measurement optical system 25, an objective measurement optical system 10, a first target projecting optical system 45, a second target projecting optical system 46, and an observing optical system 50.

<Subjective Measurement Optical System>

For example, the subjective measurement optical system 25 is used as a part of the configuration of a subjective measurer for subjectively measuring optical characteristics of the examinee's eye (as will be described in detail later). The optical characteristics of the examinee's eye may include the eye refractive power, contrast sensitivity, and binocular vision functions (such as the amount of phoria and stereoscopic function). In the present embodiment, the subjective measurer for measuring the eye refractive power of the examinee's eye will be described by way of example. The subjective measurement optical system 25 includes a light projecting optical system (target light projecting system) 30, a corrective optical system 60, and a correction optical system 90.

For example, the light projecting optical system 30 projects a target light flux toward the examinee's eye E. The light projecting optical system 30 is provided with, e.g., a display 31, a light projecting lens 33, a light projecting lens 34, a reflective mirror 36, a dichroic mirror 35, a dichroic mirror 29, and an objective lens 14. For example, the target light flux projected from the display 31 is projected toward the examinee's eye E via a plurality of optical members including the light projecting lens 33, the light projecting lens 34, the reflective mirror 36, the dichroic mirror 35, the dichroic mirror 29, and the objective lens 14 in that order.

On the display 31, there may be displayed an examination target, such as a Landolt ring target, or a fixation target for fixating the examinee's eye E (as used during subjective measurement, for example, which will be described later). For example, the target light flux from the display 31 is projected toward the examinee's eye E. The display 31 may be provided by a liquid crystal display (LCD) or an organic electro luminescence (EL). In the present embodiment, an LCD is used as the display 31 by way of example, as will be described below.

In the present embodiment, the display 31 is used as the light source for projecting the target light flux. However, the light source is not limited to the display 31. The light source only needs to be configured to project the target light flux. For example, as the light source, a digital micromirror device (DMD) may be used. Generally, a DMD has high reflectivity and is bright so that, compared to when the display 31 using polarization (liquid crystal display) is used, the amount of light of the target light flux can be maintained. The light source may also have a configuration including a visible light source for target presentation, and a target plate with a fixation target. In this case, the target plate is a rotatable disc plate with a plurality of targets, for example. The plurality of targets include, for example, a fixation target for fogging the examinee's eye E at the time of subjective measurement as will be described below, and a visual acuity examination target used for objective measurement. For example, as the visual acuity examination target, targets for visual acuity values (targets corresponding to the visual acuity values of 0.1, 0.3, . . . , and 1.5) are prepared. The targets are switched on the optical axis L2 of the light projecting optical system 30 as the target plate is rotated by means of a motor, for example. The target light flux of the target as it is illuminated by the visible light source for target presentation travels toward the examinee's eye E via the optical members from the light projecting lens 33 to the dichroic mirror 29.

The corrective optical system 60 is provided with an astigmatism corrective optical system 63 and a drive mechanism 39, for example.

The astigmatism corrective optical system 63 is disposed between the light projecting lens 34 and the light projecting lens 33, for example. The astigmatism corrective optical system 63 is used, e.g., to correct the target light flux in accordance with the cylindrical diopter power, cylindrical axis and the like of the examinee's eye. The astigmatism corrective optical system 63 is provided with, e.g., two positive cylindrical lenses 61*a* and 61*b* having mutually equal focal distances. The cylindrical lenses 61*a* and 61*b* are each independently rotated about the optical axis L2 as respective rotating mechanisms 62*a* and 62*b* are driven. In the present embodiment, the astigmatism corrective optical system 63 is provided with the two positive cylindrical lenses 61*a* and 61*b* by way of example. However, the astigmatism corrective optical system 63 is not limited to such configuration. The astigmatism corrective optical system 63 need only to be configured to be able to correct the target light flux in accordance with the cylindrical diopter power, cylindrical axis and the like of the examinee's eye. The astigmatism corrective optical system 63 may be configured to move a corrective lens into and out of the optical path of the light projecting optical system 30.

The display 31 is integrally moved in the direction of the optical axis L2 by, e.g., the drive mechanism 39 including a motor and a slide mechanism. For example, during subjective measurement, the display 31 is moved so as to change the target presentation position (presenting distance) optically with respect to the examinee's eye. In this way, the target light flux is corrected in accordance with the spherical refractive power (spherical power) of the examinee's eye. That is, a spherical power corrective optical system includes a movable display 31. For example, during the objective measurement, the display 31 is moved so as to fog the examinee's eye E. The spherical power corrective optical system is not limited to the above configuration. The spherical power corrective optical system may include a number of optical elements, and be configured to correct the target light flux by disposing the optical elements in the optical path. The spherical power corrective optical system may also be configured to move a lens disposed on the optical path in the optical axis direction.

In the present embodiment, the corrective optical system corrects, by way of example, the target light flux in accordance with the spherical power, cylindrical diopter power, and cylindrical axis of the examinee's eye. However, the corrective optical system is not limited to such configuration. For example, the corrective optical system for correcting the target light flux in accordance with the prism value of the examinee's eye may be provided. By providing the corrective optical system that corrects the target light flux in accordance with the prism value, it becomes possible to correct the target light flux so that the target light flux can be projected onto the examinee's eye even in the case of an examinee with heterophoria.

In the present embodiment, the configuration has been described, by way of example, in which the astigmatism corrective optical system 63 for cylindrical diopter power and cylindrical axis, and the spherical power corrective optical system (for example, the drive mechanism (driver) 39) are separately provided. However, this is not a limitation, and there may be provided a corrective optical system that corrects the target light flux in accordance with the spherical power, cylindrical diopter power, and cylindrical axis of the examinee's eye. The corrective optical system may be, e.g., an optical system that modulates wavefront. The corrective optical system may be, e.g., an optical system that corrects the target light flux in accordance with the spherical power, cylindrical diopter power, cylindrical axis and the like of the examinee's eye. In this case, for example, the corrective optical system may be provided with a lens disc including a number of optical elements (such as a spherical lens, a cylindrical lens, and a dispersing prism) disposed on the same circumference. In this case, as the lens disc is rotated and controlled by a driver (such as an actuator), an optical element desired by the examiner is disposed on the optical axis L2.

As the optical element (such as a cylindrical lens, a cross cylinder lens, or a rotary prism) disposed on the optical axis L2 is rotated and controlled by the driver, the optical element is disposed on the optical axis L2 at a rotation angle desired by the examiner. The switching and the like of the optical elements disposed on the optical axis L2 may be performed by the examiner operating an input unit (operation unit), such as the monitor 4.

Either one or a plurality of lens discs may be used. When a plurality of lens discs is disposed, a driver corresponding to each of the lens discs may be provided. For example, each lens disc is provided with an opening (or a 0 D lens) and a plurality of optical elements, forming a lens disc group. Representative types of the lens discs are a spherical lens disc including a plurality of spherical lenses with different powers; a cylindrical lens disc including a plurality of cylindrical lenses with different powers; and an auxiliary lens disc including a plurality of types of auxiliary lenses. In the auxiliary lens disc, at least a red filter/green filter, a prism, a cross cylinder lens, a polarization plate, a Maddox lens, or an auto cross cylinder lens is disposed. The cylindrical lenses are disposed so as to be rotatable by the driver about the optical axis L2. The rotary prism and the cross cylinder lens may be disposed so as to be rotatable by the driver about the respective optical axes.

The correction optical system 90 is disposed, e.g., between the objective lens 14 and a deflecting mirror 81 (see FIG. 3), which will be described later. The correction optical system 90 is used for correcting optical aberration caused in the subjective measurer, for example. For example, the correction optical system 90 is used for correcting astigmatism, among other optical aberrations, caused in the subjective measurer. The correction optical system 90 is provided with two positive cylindrical lenses 91*a* and 91*b* having an equal focal distance, for example. The correction optical system 90 corrects the astigmatism by, e.g., adjusting cylindrical diopter power and cylindrical axis. The cylindrical lenses 91*a* and 91*b* are each independently rotated about an optical axis L3 by the driving of rotating mechanisms 92*a* and 92*b*, respectively. In the present embodiment, the correction optical system 90 is provided with the two positive cylindrical lenses 91*a* and 91*b* by way of example. However, this is not a limitation; the correction optical system 90 needs only to be configured to be able to correct astigmatism. For example, the correction optical system 90 may be configured to move a correction lens into and out of the optical axis L3. In the present embodiment, the correction optical system 90 is disposed as a separate member from the corrective optical system 60. However, this is merely by way of example and not of limitation, and the corrective optical system 60 may also serve as the correction optical system 90. In this case, the cylindrical diopter power and cylindrical axis of the examinee's eye will be corrected in accordance with the amount of astigmatism. That is, the corrective optical system 60 is driven so as to correct the target light flux in accordance with the cylindrical diopter power and cylindrical axis of the examinee's eye, in light of (while correcting) the amount of astigmatism. When the corrective optical system 60 thus also serves as the correction optical system 90, the need for a separate correction optical system for optical aberration is eliminated, in addition to making complex control unnecessary. Accordingly, optical aberration can be corrected in a simple configuration.

<Objective Measurement Optical System>

For example, the objective measurement optical system 10 is used as a part of the configuration of an objective measurer for objectively measuring the optical characteristics of the examinee's eye (as will be described in detail later). Examples of the optical characteristics of the examinee's eye include eye refractive power, ocular axial length, and corneal shape. In the present embodiment, the objective measurer for measuring the eye refractive power of the examinee's eye will be described by way of example.

The objective measurement optical system 10 is provided with, e.g., a projecting optical system 10*a*, a light receiving optical system 10*b*, and a correction optical system 90. The projecting optical system (light projecting optical system) 10*a* projects a spot of measurement target onto the fundus of the examinee's eye E, via the pupil center portion of the examinee's eye E, for example. The light receiving optical system 10*b* obtains fundus reflected light, produced by optical reflection by the fundus, in the form of a ring-shaped fundus reflection image via the pupil peripheral portion, for example. The light receiving optical system 10*b* causes the ring-shaped fundus reflection image to be captured by a two-dimensional imaging device 22.

The projecting optical system 10*a* includes a measurement light source (light source) 11, a relay lens 12, a hole mirror 13, a prism 15, a driver (motor) 23, a dichroic mirror 35, a dichroic mirror 29, and an objective lens 14, e.g., which are disposed on the optical axis L1 of the objective measurement optical system 10. The prism 15 is a light flux deflecting member, for example. The driver 23 is a rotator for rotationally driving the prism 15 about the optical axis L1, for example. The light source 11 is in a conjugate relation with the fundus of the examinee's eye, for example. A hole portion of the hole mirror 13 is in a conjugate relation with the pupil, for example. The prism 15 is positioned away from the conjugate position with the pupil of the examinee's eye E, for example. For example, the prism 15 makes the light flux passing therethrough eccentric with respect to the optical axis L1. Instead of the prism 15, parallel flat plates as a light flux deflecting member may be disposed diagonally on the optical axis L1.

The dichroic mirror 35 makes the optical path of the subjective measurement optical system 25 and the optical path of the objective measurement optical system 10 common, for example. That is, the dichroic mirror 35 makes the optical axis L2 of the subjective measurement optical system 25 and the optical axis L1 of the objective measurement optical system 10 coaxial. The dichroic mirror (beam splitter) 29, which is an optical path diverting member, reflects the light flux due to the subjective measurement optical system 25 and the measurement light due to the projecting optical system 10*a*, and guides them to the examinee's eye.

The light receiving optical system 10*b* shares the objective lens 14, the dichroic mirror 29, the dichroic mirror 35, the prism 15, and the hole mirror 13 with the projecting optical system 10*a*, for example. The light receiving optical system 10*b* is provided with: a relay lens 16 and a mirror 17, which are disposed on the optical path in the reflecting direction of the hole mirror 13; and a light receiving aperture 18, a collimator lens 19, a ring lens 20, and a two-dimensional imaging device 22 (hereafter referred to as an imaging device 22), such as a CCD, which are disposed on the optical path in the reflecting direction of the mirror 17. For example, the light receiving aperture 18 and the imaging device 22 are in a conjugate relation with the fundus of the examinee's eye. The ring lens 20 is provided with, e.g., a ring-shaped lens portion and a light shielding portion. The light shielding portion is the region other than the lens portion. The light shielding portion is provided with a light shielding coating. The ring lens 20 is in an optically conjugate positional relationship with the pupil of the examinee's eye. An output signal from the imaging device 22 is received by the calculation controller 70 (hereafter referred to as a controller 70), for example.

The dichroic mirror 29 reflects reflected light (fundus reflected light) which is obtained as the measurement light from the projecting optical system 10*a* is reflected by the fundus of the examinee's eye, toward the light receiving optical system 10*b*, for example. The dichroic mirror 29 also transmits anterior segment observation light and alignment light and guides them to the observing optical system 50, for example. The dichroic mirror 35 reflects the fundus reflected light toward the light receiving optical system 10*b*, for example.

The configuration of the objective measurement optical system 10 is not limited to the above configuration. The objective measurement optical system 10 may have other known configurations. For example, the objective measurement optical system 10 may be configured to project a ring-shaped measurement target from the pupil peripheral portion onto the fundus. In this case, in the objective measurement optical system 10, a ring-shaped fundus reflected light obtained from the pupil center portion may be received by the two-dimensional imaging device 22.

The configuration of the objective measurement optical system 10 is not limited to the above configuration. The objective measurement optical system 10 may be any measurement optical system including a light projecting optical system and a light receiving optical system. The light projecting optical system projects the measurement light toward the fundus of the examinee's eye. The light receiving optical system receives, using a photo detector, the reflected light that is obtained through reflection of the measurement light by the fundus. For example, an eye refractive power measurement optical system may be provided with a Shack-Hartmann sensor. Of course, apparatuses of other measurement systems (such as an apparatus of phase differential system whereby a slit is projected) may be utilized.

The light source 11 of the projecting optical system 10*a*, the light receiving aperture 18, collimator lens 19, ring lens 20, and imaging device 22 of the light receiving optical system 10*b* are integrally movable in the optical axis direction, for example. In the present embodiment, the light source 11 of the projecting optical system 10*a*, and the light receiving aperture 18, collimator lens 19, ring lens 20, and imaging device 22 of the light receiving optical system 10*b* are integrally moved in the direction of the optical axis L1 by the drive mechanism 39 for driving the display 31. That is, the display 31, the light source 11 of the projecting optical system 10*a*, and the light receiving aperture 18, collimator lens 19, ring lens 20, and imaging device 22 of the light receiving optical system 10*b* are synchronized and integrally moved as a drive unit 95. Of course, these members may be configured to be each separately driven.

For example, the drive unit 95 moves a part of the objective measurement optical system 10 in the optical axis direction so that an outer ring of light flux can enter the imaging device 22 with respect to each meridian direction. That is, by moving a part of the objective measurement optical system 10 in the optical axis L1 direction in accordance with the spherical refractive error (spherical refractive power) of the examinee's eye, the spherical refractive error is corrected. In addition, the light source 11, the light receiving aperture 18, and the imaging device 22 are thereby made optically conjugate with respect to the fundus of the examinee's eye. The position to which the drive mechanism 39 is moved may be detected by a potentiometer, which is not illustrated. The hole mirror 13 and the ring lens 20 are disposed so as to become conjugated with the pupil of the examinee's eye at a certain magnification ratio, regardless of the amount of movement of the part of the objective measurement optical system 10 (movable unit).

In the above configuration, the measurement light emitted from the light source 11 passes through the relay lens 12, the hole mirror 13, the prism 15, the dichroic mirror 35, the dichroic mirror 29, and the objective lens 14, and forms a spot of a point light source image on the fundus of the examinee's eye. In this case, by the prism 15 rotated about the optical axis, the pupil-projected image of the hole portion of the hole mirror 13 (the light flux projected on the pupil) is eccentrically rotated at high speed. The point light source image projected on the fundus is reflected or scattered, exits the examinee's eye, and is then condensed by the objective lens 14. Thereafter, the light passes through the dichroic mirror 29, the dichroic mirror 35, the prism 15 being rotated at high speed, the hole mirror 13, the relay lens 16, and the mirror 17, and is again condensed at the position of the light receiving aperture 18. As the condensed light passes through the collimator lens 19 and the ring lens 20, a ring-shaped image is formed on the imaging device 22.

The prism 15 is disposed on the common optical path of the projecting optical system 10*a* and the light receiving optical system 10*b*. Accordingly, the reflected light flux from the fundus passes through the same prism 15 as the prism through which the light flux of the projecting optical system 10*a* passes. Accordingly, in the optical system subsequent to the prism 15, an inverted scan is implemented as if there were no eccentricity between the projected light flux and the reflected light flux (received light flux) on the pupil.

The objective measurement optical system 10 shares the correction optical system 90 with the subjective measurement optical system 25. Of course, a separate correction optical system may be provided for the objective measurement optical system 10.

<First Target Projecting Optical System and Second Target Projecting Optical System>

In the present embodiment, the first target projecting optical system 45 and the second target projecting optical system 46 are disposed between the correction optical system 90 and the deflecting mirror 81. The locations of the first target projecting optical system 45 and the second target projecting optical system 46, however, are of course not limited to such positions.

In the first target projecting optical system 45, a plurality of infrared light sources is disposed concentrically at 45° intervals about the optical axis L3. The plurality of infrared light sources is disposed so as to be right-left symmetric across a vertical plane passing the optical axis L3. The first target projecting optical system 45 emits near-infrared light for projecting the alignment target onto the cornea of the examinee's eye. The second target projecting optical system 46 is disposed at a different position from the first target projecting optical system 45, and provided with six infrared light sources. In this case, the first target projecting optical system 45 is configured to project a target at infinity onto the cornea of the examinee's eye E, from the right and left directions. The second target projecting optical system 46 is configured to project a target at a finite distance onto the cornea of the examinee's eye E from upper and lower directions, or from oblique directions. For convenience of description, FIG. 2 only illustrates a part of the first target projecting optical system 45 and only a part of the second target projecting optical system 46. The second target projecting optical system 46 is also used to provide anterior segment illumination for illuminating the anterior segment of the examinee's eye. The second target projecting optical system 46 may also be utilized as a target for corneal shape measurement. The light source for the first target projecting optical system 45, and the light source for the second target projecting optical system 46 are not limited to point light sources. The light sources may be ringed light sources or linear light sources, for example.

<Observing Optical System>

The observing optical system (imaging optical system) 50 shares the objective lens 14 and the dichroic mirror 29 with the subjective measurement optical system 25 and the objective measurement optical system 10. In addition, the observing optical system 50 is provided with an imaging lens 51 and the two-dimensional imaging device 52. The two-dimensional imaging device 52 has an imaging surface disposed, e.g., at a substantially conjugate position with respect to the anterior segment of the examinee's eye. For example, an output signal from the two-dimensional imaging device 52 is received by the controller 70. In this way, an image of the anterior segment of the examinee's eye is captured by the two-dimensional imaging device 52 and displayed on the monitor 4. The observing optical system 50 also serves as an optical system for detecting an alignment target image formed by the first target projecting optical system 45 and the second target projecting optical system 46 on the cornea of the examinee's eye. The position of the alignment target image is detected by the controller 70.

<Internal Configuration of Subjective Optometry Apparatus>

Figure 3:
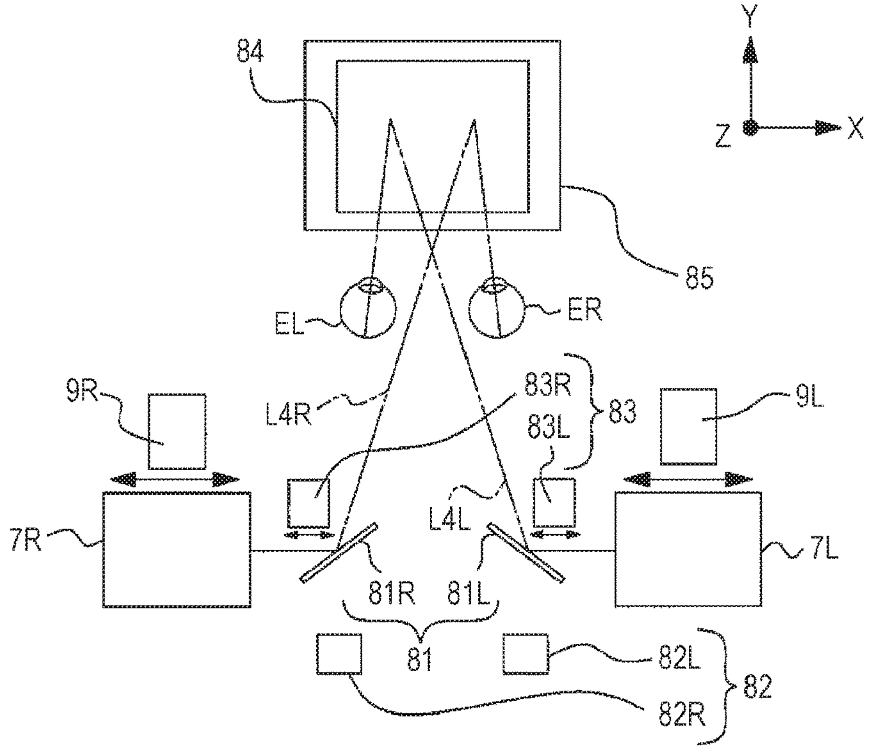
FIG. 3 is a schematic configuration diagram of the interior of the subjective optometry apparatus according to the present embodiment as viewed from the front.
Figure 4:
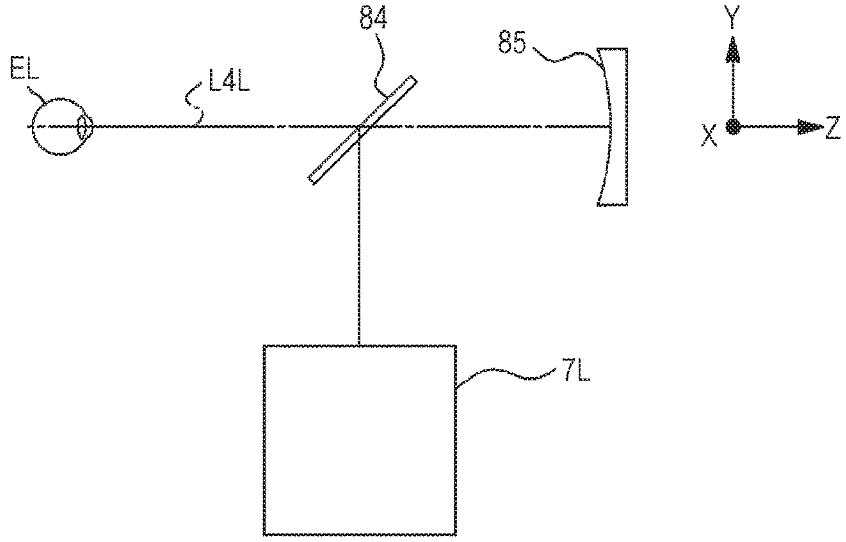
FIG. 4 is a schematic configuration diagram of the interior of the subjective optometry apparatus according to the present embodiment as viewed from the side.
Figure 5:
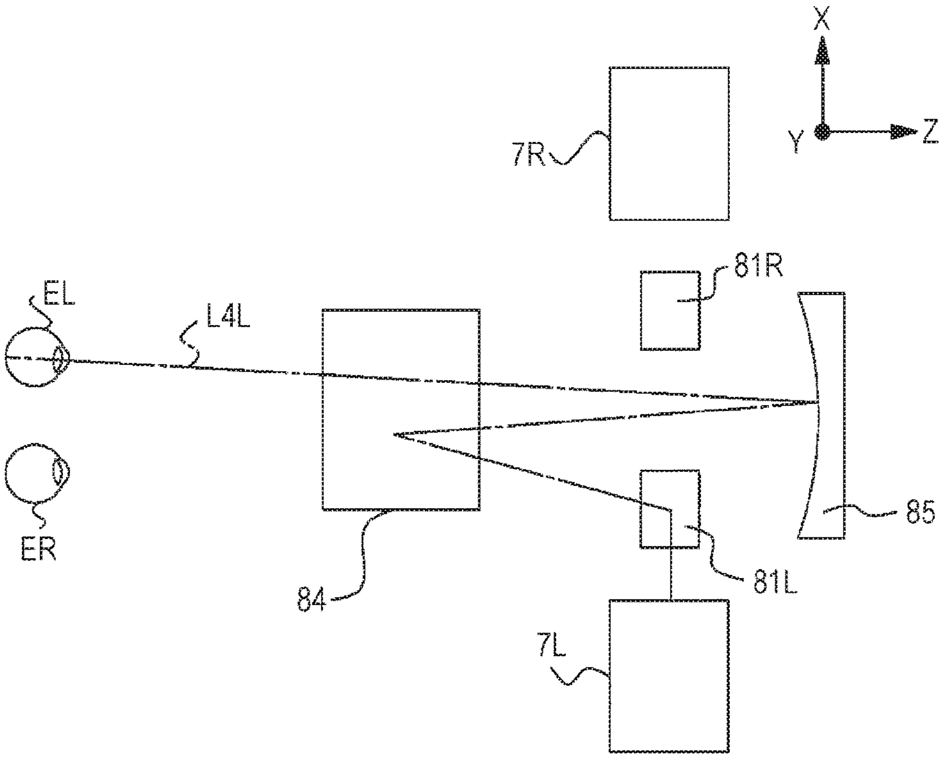
FIG. 5 is a schematic configuration diagram of the interior of the subjective optometry apparatus according to the present embodiment as viewed from the top.

The internal configuration of the subjective optometry apparatus 1 will be described. FIG. 3 is a schematic configuration diagram of the interior of the subjective optometry apparatus 1 according to the present embodiment, as viewed from the front (from direction A in FIG. 1). FIG. 4 is a schematic configuration diagram of the interior of the subjective optometry apparatus 1 according to the present embodiment, as viewed from the side (from direction B in FIG. 1). FIG. 5 is a schematic configuration diagram of the interior of the subjective optometry apparatus 1 according to the present embodiment, as viewed from the top (from direction C in FIG. 1). In FIG. 3, for convenience of description, the optical axis of the reflected light by the half mirror 84 is omitted. In FIG. 4, for convenience of description, the optical axis of the left-eye measurer 7L is illustrated whereas the optical axis of the right-eye measurer 7R is omitted. In FIG. 5, the optical axis of the left-eye measurer 7L is illustrated whereas the optical axis of the right-eye measurer 7R is omitted for convenience of description.

The subjective optometry apparatus 1 is provided with the subjective measurer and the objective measurer, for example. The subjective measurer is provided with the measurer 7, the deflecting mirror 81, a driver 83, a driver 82, a half mirror 84, and a concave mirror 85. Of course, the configuration of the subjective measurer is not limited to such configuration. For example, the objective measurer is provided with the measurer 7, the deflecting mirror 81, the half mirror 84, and the concave mirror 85. Of course, the configuration of the objective measurer is not limited to such configuration.

The subjective optometry apparatus 1 includes a right-eye driver 9R and a left-eye driver 9L. The right-eye driver 9R and the left-eye driver 9L are respectively capable of moving the right-eye measurer 7R and the left-eye measurer 7L in the X-direction. For example, by moving the right-eye measurer 7R and the left-eye measurer 7L, the distance between the deflecting mirror 81 and the measurer 7 is changed. As a result, the presentation position of the target light flux in the Z-direction is changed. In this way, the target light flux corrected by the corrective optical system 60 can be guided to the examinee's eye. That is, the position of the corrected target light flux in the Z-direction can be adjusted so that the image of the target light flux corrected by the corrective optical system 60 can be formed at the fundus of the examinee's eye.

The deflecting mirror 81 includes, e.g., a pair of a right-eye deflecting mirror 81R and a left-eye deflecting mirror 81L that are respectively disposed on the right and left. The deflecting mirror 81 is disposed between the corrective optical system 60 and the examinee's eye, for example. That is, the corrective optical system 60 includes a right-left pair of a right-eye corrective optical system and a left-eye corrective optical system. The right-eye deflecting mirror 81R is disposed between the right-eye corrective optical system and the right eye ER. The left-eye deflecting mirror 81L is disposed between the left-eye corrective optical system and the left eye EL. Preferably, the deflecting mirror 81 is disposed at a conjugate position with respect to the pupil, for example.

The right-eye deflecting mirror 81R reflects and guides the light flux projected from the right-eye measurer 7R to the right eye ER, for example. The right-eye deflecting mirror 81R also reflects and guides reflected light obtained by optical reflection by the right eye ER to the right-eye measurer 7R, for example. The left-eye deflecting mirror 81L reflects and guides the light flux projected from the left-eye measurer 7L to the left eye EL, for example. The left-eye deflecting mirror 81L also reflects and guides reflected light obtained by optical reflection by the left eye EL to the left-eye measurer 7L, for example. In the present embodiment, the deflecting mirror 81 is illustrated as an example of the deflecting member for reflecting and guiding the light flux projected from the measurer 7 to the examinee's eye E. However, the deflecting member is not limited to the deflecting mirror 81. The deflecting member may be any member capable of reflecting and guiding the light flux projected from the measurer 7 to the examinee's eye E. Examples of the deflecting member include a prism and a lens.

The driver 83 is provided with a motor (driver) and the like, for example. The driver 83 includes, e.g., a driver 83R for driving the right-eye deflecting mirror 81R, and a driver 83L for driving the left-eye deflecting mirror 81L. Through the driving of the driver 83, the deflecting mirror 81 can be moved in the X-direction, for example. As the right-eye deflecting mirror 81R and the left-eye deflecting mirror 81L are moved, for example, the distance between the right-eye deflecting mirror 81R and the left-eye deflecting mirror 81L is modified. In this way, the distance between the right-eye optical path and the left-eye optical path in the X-direction can be modified in accordance with the interpupillary distance of the examinee's eyes.

The driver 82 is provided with a motor (driver) and the like, for example. The driver 82 includes, by way of example, a driver 82R for driving the right-eye deflecting mirror 81R, and a driver 82L for driving the left-eye deflecting mirror 81L. The driver 82 is driven, e.g., to move the deflecting mirror 81 rotationally. For example, the driver 82 causes the deflecting mirror 81 to rotate with respect to a rotational axis in the horizontal direction (the X-direction) and a rotational axis in the vertical direction (Y-direction). That is, the driver 82 causes the deflecting mirror 81 to rotate in the X- and Y-directions. The rotating direction of the deflecting mirror 81 may be one of the horizontal direction or the vertical direction. A plurality of deflecting mirrors may be provided on each of the right-eye optical path and the left-eye optical path. For example, two deflecting mirrors may be provided on each of the right-eye optical path and the left-eye optical path. For example, two deflecting mirrors may be provided on the right-eye optical path. In this case, one deflecting mirror may be rotated in the X-direction, and the other deflecting mirror may be rotated in the Y-direction. As the deflecting mirror 81 is rotationally moved, the apparent light flux formed in front of the examinee's eye can be deflected. In this way, the formation position of the image generated by the corrective optical system 60 can be optically corrected.

The concave mirror 85 is shared by the right-eye measurer 7R and the left-eye measurer 7L, for example. For example, the concave mirror 85 is shared by a right-eye optical path including the right-eye corrective optical system, and a left-eye optical path including the left-eye corrective optical system. Specifically, the concave mirror 85 is disposed at a position passing both the right-eye optical path including the right-eye corrective optical system, and the left-eye optical path including the left-eye corrective optical system. Of course, the concave mirror 85 may not be configured to be shared by the optical paths. A concave mirror may be provided for each of the right-eye optical path including the right-eye corrective optical system, and the left-eye optical path including the left-eye corrective optical system. The concave mirror 85 guides the target light flux that has passed through the corrective optical system to the examinee's eye, and forms an image of the target light flux, having passed through the corrective optical system, in front of the examinee's eye, for example. In the present embodiment, the configuration includes the use of the concave mirror 85. However, this is merely by way of example and, instead of the concave mirror 85, various optical members may be used. For example, a lens or a planar mirror may be used as the optical member.

The concave mirror 85 is used commonly for the subjective measurer and the objective measurer, for example. For example, the target light flux projected from the subjective measurement optical system 25 is projected onto the examinee's eye via the concave mirror 85. In addition, for example, the measurement light projected from the objective measurement optical system 10 is projected onto the examinee's eye via the concave mirror 85. In addition, for example, the reflected light of the measurement light projected from the objective measurement optical system 10 is guided to the light receiving optical system 10*b* of the objective measurement optical system 10 via the concave mirror 85. In the present embodiment, the reflected light of the measurement light projected from the objective measurement optical system 10 is guided to the light receiving optical system 10*b* of the objective measurement optical system 10 via the concave mirror 85. However, this is merely by way of example, and the reflected light of the measurement light projected from the objective measurement optical system 10 may be guided to the light receiving optical system 10*b* of the objective measurement optical system 10 not via the concave mirror 85.

More specifically, in the present embodiment, at least the optical axis between the concave mirror 85 and the examinee's eye E in the subjective measurer and the optical axis between the concave mirror 85 and the examinee's eye E in the objective measurer are coaxial, for example. In the present embodiment, the optical axis L2 of the subjective measurement optical system 25 and the optical axis L1 of the objective measurement optical system 10 are combined by the dichroic mirror 35. Accordingly, the optical axis L2 and the optical axis L1 are coaxial.

In the following, the optical path of the subjective measurer will be described. For example, the subjective measurer reflects the target light flux that has passed through the corrective optical system 60 toward the examinee's eye, using the concave mirror 85, thereby guiding the target light flux to the examinee's eye. The subjective measurer forms an image of the target light flux, having passed through the corrective optical system 60, in front of the examinee's eye so that the distance sensed by the examinee to exist between the formation position of the image and the examinee's eye becomes an optically predetermined examination distance.

That is, the concave mirror 85 reflects the target light flux so as to become substantially parallel light fluxes. Accordingly, for the examinee, it appears as if the target image is located farther than the actual distance between the examinee's eye E and the display 31. That is, the use of the concave mirror 85 enables the target image to be presented to the examinee as if the image of the target light flux (target image) were located at a position corresponding to the predetermined examination distance.

The optical path of the subjective measurer will be described in greater detail. In the following description, the left-eye optical path will be described by way of example. The right-eye optical path has a similar configuration to the left-eye optical path. For example, in the left-eye subjective measurer, the target light flux projected from the display 32 of the left-eye measurer 7L enters the astigmatism corrective optical system 63 via the light projecting lens 33. The target light flux that has passed through the astigmatism corrective optical system 63 enters the correction optical system 90 via the reflective mirror 36, the dichroic mirror 35, the dichroic mirror 29, and the objective lens 14. The target light flux that has passed through the correction optical system 90 is emitted from the left-eye measurer 7L, and projected onto the left-eye deflecting mirror 81L. The target light flux emitted from the left-eye measurer 7L and reflected by the left-eye deflecting mirror 81 is then reflected by the half mirror 84 toward the concave mirror 85. The target light flux reflected by the concave mirror passes through the half mirror 84 and reaches the left eye EL.

In this way, with reference to the eyeglass wearing position for the left eye EL (for example, approximately 12 mm from the corneal apex), the target image corrected by the corrective optical system 60 is formed on the fundus of the left eye EL. This is as if the astigmatism corrective optical system 63 were disposed in front of the eye, and as if the adjustment of the spherical power by the spherical power corrective optical system (in the present embodiment, by the driving of the drive mechanism 39) were performed in front of the eye. Thus, the examinee can sight the target image in a natural state via the concave mirror 85. In the present embodiment, the right-eye optical path has a similar configuration to the left-eye optical path. With reference to the eyeglass wearing positions (such as approximately 12 mm from the corneal apex) for both of the examinee's eyes ER and EL, the target images corrected by the right-left pair of corrective optical systems 60 are formed on the fundi of the examinee's eyes. In this way, the examinee responds to the examiner while directly gazing at the target in a natural visual state. The correction by the corrective optical system 60 is implemented until the examinee can properly see the examination target. Based on the corrective value, the optical characteristics of the examinee's eye are subjectively measured.

The optical path of the objective measurer will be described next. In the following description, the left-eye optical path will be described by way of example. The right-eye optical path has a similar configuration to the left-eye optical path. In the left-eye objective measurer, for example, the measurement light emitted from the light source 11 of the projecting optical system 10*a* in the objective measurement optical system 10 enters the correction optical system 90 via the relay lens 12 to the objective lens 14. The measurement light that has passed through the correction optical system 90 is emitted from the left-eye measurer 7L, and projected onto the left-eye deflecting mirror 81L. The measurement light emitted from the left-eye measurer 7L and reflected by the left-eye deflecting mirror 81 is reflected by the half mirror 84 toward the concave mirror 85. The measurement light reflected by the concave mirror passes through the half mirror 84 and reaches the left eye EL, forming a spot of point light source image on the fundus of the left eye EL. In this case, the pupil-projected image due to the hole portion of the hole mirror 13 (projected light flux on the pupil) is eccentrically rotated at high speed by the prism 15 rotated about the optical axis.

The light of the point light source image formed on the fundus of the left eye EL is reflected and scattered by the left eye EL and then exits the left eye EL. The light travels along the optical path that has been traveled by the measurement light, and is condensed by the objective lens 14. The condensed light passes through the dichroic mirror 29, the dichroic mirror 35, the prism 15, the hole mirror 13, and the relay lens 16, and is then reflected by the mirror 17. The reflected light from the mirror 17 is again condensed at the opening of the light receiving aperture 18. The condensed light is further made into substantially parallel light fluxes (in the case of emmetropic eye) by the collimator lens 19. The substantially parallel light fluxes are extracted by the ring lens 20 in the form of a ring-shaped light flux. The ring-shaped light flux is received by the imaging device 22 in the form of a ring image. By analyzing the received ring image, the optical characteristics of the examinee's eye can be measured objectively.

Thus, in the subjective optometry apparatus 1 according to the present embodiment, an image of the corrective optical system is formed in front of the examinee's eye, for example. The subjective optometry apparatus 1 according to the present embodiment includes the objective measurer as well as the subjective measurer. Accordingly, the subjective optometry apparatus 1 can perform subjective measurement and objective measurement in an open state without disposing the corrective optical system in front of the examinee's eye. In this way, the measurements can be performed in a natural state as if the examinee is seeing an object in daily life, whereby the measurements can be performed in a satisfactory manner. In addition, because the objective measurement of optical characteristics and the subjective measurement of optical characteristics can be performed by a single apparatus, the optical characteristics of the examinee's eye can be smoothly measured.

In addition, in the subjective optometry apparatus 1 according to the present embodiment, the subjective measurer and the objective measurer share optical members. In this way, the number of members can be decreased, enabling the subjective optometry apparatus 1 to be constructed in a simple configuration. Further, excess space can be decreased, so that the size of the subjective optometry apparatus 1 can be reduced.

For example, in the subjective optometry apparatus 1 according to the present embodiment, the optical axis between the optical members and the examinee's eye in the subjective examination unit, and the optical axis between the optical members and the examinee's eye in the objective examination unit are coaxial. Accordingly, when measuring the examinee's eye, by adjusting one examination unit, adjustment of the other examination unit can also be completed. Thus, the examination unit can be adjusted easily at the time of measurement. That is, by adjusting the objective measurer, the adjustment of the subjective measurer can also be easily performed.

In the subjective optometry apparatus 1 according to the present embodiment, the target light flux is made into substantially parallel light fluxes by means of the concave mirror 85, for example. Accordingly, the subjective measurer can present the target to the examinee as if the target were located at a position corresponding to the optically predetermined examination distance (predetermined examination position). Accordingly, it becomes unnecessary actually to dispose members and the like so as to present the target at the predetermined examination position. In this way, excess members and space can be eliminated, whereby the size of the subjective optometry apparatus 1 can be decreased.

<Controller>

The controller 70 is provided with a CPU (processor), a RAM, and a ROM, for example. For example, the CPU of the controller 70 controls the various members of the subjective optometry apparatus 1. For example, the RAM temporarily stores various information. In the ROM of the controller 70, various programs for controlling the operation of the subjective optometry apparatus 1, target data for various examinations, initial values and the like are stored. The controller 70 may be provided with a plurality of CPUs.

To the controller 70, a nonvolatile memory (storage) 72, a monitor 4 (which, in the present embodiment, also serves as an operating unit), and various members are electrically connected. The nonvolatile memory (hereafter referred to as the memory) 72 is a non-transitory storage medium capable of retaining stored content even when power supply is turned off. Examples of the memory 72 include a hard disk drive, a flash ROM, an OCT device, and a USB memory detachably mounted to the subjective optometry apparatus 1. In the memory 72, a control program for controlling the subjective measurer and the objective measurer is stored, for example.

<Modification of Convergence Angle by Adjustment of Deflecting Angle with Respect to Concave Mirror>

In the present embodiment, the controller 70 may control the light deflecting members (for example, the deflecting mirrors 81R and 81L) respectively disposed on the right-eye optical path and the left-eye optical path, so as to change the deflecting angle of a right-eye measurement optical axis L4R and a left-eye measurement optical axis L4L with respect to the horizontal direction. For example, the controller (convergence angle modifier) 70 may modify the incidence angle of the measurement optical axes L4R and L4L with respect to the concave mirror 85, so as to modify the convergence angle of the target light flux emitted from the right-eye optical path and the left-eye optical path. In this way, the convergence angle can be appropriately modified in accordance with the target presenting distance.

Figure 6:
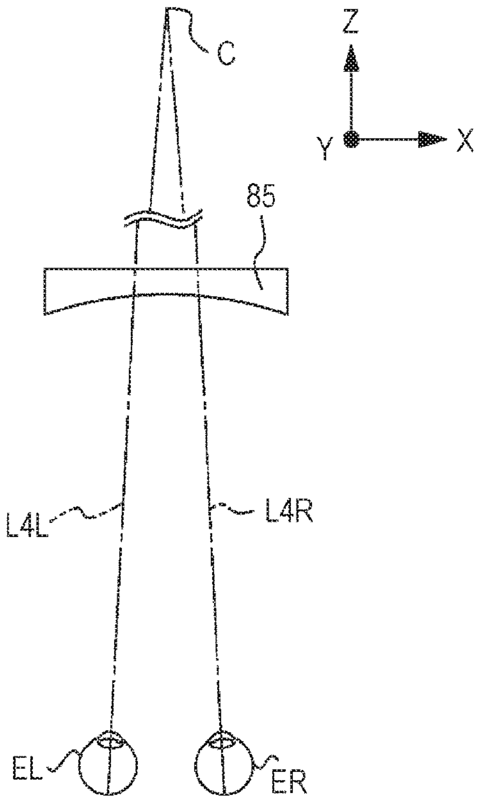
FIG. 6 illustrates an example of presentation of a target at a far distance.
Figure 7:
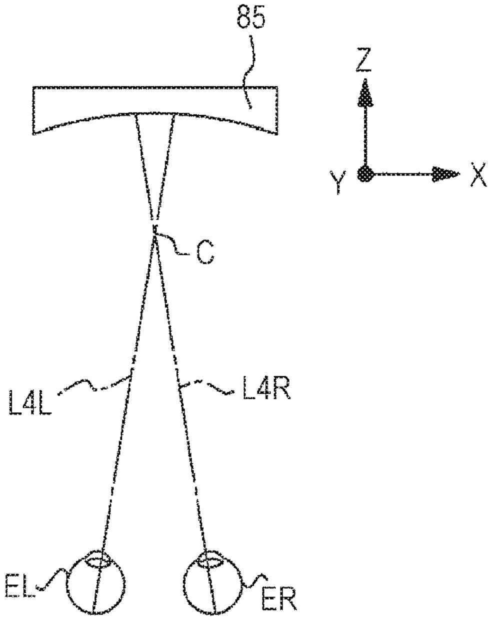
FIG. 7 illustrates an example of presentation of a target at a short distance.

In this case, the angles of the measurement optical axes L4R and L4L are modified with respect to the horizontal direction (the X-direction), whereby the position of the intersecting point C of the right-eye measurement optical axis L4R and the left-eye measurement optical axis L4L is modified (see FIG. 6 and FIG. 7). The target light flux from the right-eye measurer 7R is projected onto the right eye ER, with a main light ray corresponding to the measurement optical axis L4R. Accordingly, the direction of the visual line of the right eye ER becomes coaxial with the right-eye measurement optical axis L4R. Similarly, the target light flux from the left-eye measurer 7L is projected onto the left eye EL with a main light ray corresponding to the left-eye measurement optical axis L4L. Accordingly, the direction of the visual line of the left eye EL becomes coaxial with the left-eye measurement optical axis L4L. As a result, the convergence angle of the target light flux is modified, and the convergence angle of the right-left eye is modified.

More specifically, the controller 70 may alter (modify) the deflecting angle of the measurement optical axes L4R and L4L by controlling the driver 82 and thereby adjusting the reflecting angles of the deflecting mirrors 81R and 81L. Of course, the deflecting mirrors 81R and 81L are not intended to be a limitation, and other light deflecting members may be used.

FIG. 6 illustrates an example of presentation of a target at a far distance. For example, the controller 70 may set a convergence angle corresponding to the far distance by deflecting the measurement optical axes L4R and L4L such that the measurement optical axes L4R and L4L pass the focus position of the concave mirror 85. The optical axes may not pass the exact focus position; the convergence angle only needs to correspond to the far distance.

For example, the measurement optical axes L4R and L4L after reflection by the concave mirror 85 have a mutually parallel relationship, and lie in the same direction as the Z-direction. The intersecting point C is formed at infinity or a far position (such as 5 m away from the examinee's eye apparently). The far position is a target presentation position in the case of presentation of the target at a far distance, for example. In this case, the controller 70 may adjust the target presentation position so as to form the target at the far position for the examinee's eye. As a result, the target is apparently presented from afar with respect to the examinee's eye. In addition, the right and left target light fluxes are set at a convergence angle corresponding to the far distance.

FIG. 7 illustrates an example of target presentation at a short distance. For example, the controller 70 may deflect the measurement optical axes L4R and L4L so that the angle formed by the measurement optical axis L4R (L4L) and the measurement optical axis of the measurer 7R (7L) becomes even smaller than that for the far distance. In this way, the convergence angle (intersecting point C) can be shifted nearer.

For example, the controller 70 may deflect the measurement optical axes L4R and L4L so that the measurement optical axes L4R and L4L immediately before being reflected by the concave mirror 85 have a mutually parallel relationship. The measurement optical axes L4R and L4L after reflection by the concave mirror 85 pass the focus position of the concave mirror 85 and reach the right and left eyes. In this way, apparently, the intersecting point C is formed at the focus position of the concave mirror 85. In this case, the controller 70 may adjust the target presentation position so that the target is formed at a near position corresponding to the intersecting point C. As a result, apparently, the target is presented to the examinee's eye from the near position. In addition, the right and left target light fluxes are set at a convergence angle corresponding to the short distance set. The near position is a target presentation position in the case of presentation of the target at a short distance, for example.

The target presenting distance, of course, is not limited to the above distance. For example, the controller 70 may modify the convergence angle of the target light flux arbitrarily by modifying the position of the intersecting point C with respect to the examinee's eye by deflecting the measurement optical axes L4R and L4L. In this case, a correspondence relationship between the deflecting angle (drive angle) of the light deflecting member and the target presenting distance may be set in advance and stored in the memory 72. Specifically, the reflecting angle of the deflecting mirrors 81R and 81L and the target presenting distance may be associated with each other in advance. In this case, a correspondence table, a computing formula and the like may be stored in the memory 72.

The controller 70 may receive the target presenting distance, based on an operation signal from the monitor 4 (operating unit), for example. The controller 70 may also acquire a deflecting angle corresponding to the presenting distance from the memory 72. Further, the controller 70 may drive the light deflecting members so as to be disposed at an angle corresponding to the acquired deflecting angle.

As described above, by switching the deflecting angle of the measurement optical axes L4R and L4L with respect to the concave mirror 85 in accordance with a modification in the target presenting distance, target presentation can be implemented in a state close to natural view. As a result, satisfactory measurement results can be obtained.

When the target presenting distance is modified by controlling the light projecting optical system 30, the controller 70 may modify the target presenting distance by modifying the spherical power of the corrective optical system 60. For example, when the target is presented at a predetermined short distance (such as 33 cm), the controller 70, with reference to the position of the corrective power for distance vision (at the time of target presentation at a far distance), i.e., the distance corrective power determined by objective refractive power measurement for distance vision, or by visual acuity measurement for distance vision, may locate the display 31 at a position closer by the power corresponding to the short distance (for example, 3.0 D).

<PD Adjustment by Modification of Distance Between Right and Left Measurement Optical Axes>

In the present embodiment, the controller 70, by controlling the light deflecting member (for example, the deflecting mirrors 81R and 81L) disposed in each of the right-eye optical path and the left-eye optical path, may modify an inter-optical axis distance LPD between the right-eye measurement optical axis L4R and the left-eye measurement optical axis L4L with respect to the horizontal direction (the X-direction) (see FIG. 8). In this case, by adjusting the position of the respective light deflecting members with respect to the horizontal direction, based on the interpupillary distance of the examinee, the right-eye optical path and the left-eye optical path may be disposed at the positions corresponding to the interpupillary distance of the examinee (right-left eye distance). The interpupillary distance of the examinee may be acquired by determining the right-left eye distance by image processing using the above-described imaging optical system for both eyes. Alternatively, a measurement result of the interpupillary distance of the examinee that has been previously measured using a PD meter and the like may be acquired from the memory 72.

As a result, the right-left pair of measurement optical systems is disposed at the position corresponding to the interpupillary distance. For example, the measurement optical axes of the right-left pair of subjective measurement optical systems 25 are disposed at the positions corresponding to the interpupillary distance. In this way, the corrective optical system 60, the light projecting optical system 30 and the like are disposed at the positions corresponding to the interpupillary distance. In addition, the measurement optical axes of the right-left pair of objective measurement optical systems 10 are disposed at the positions corresponding to the interpupillary distance. The adjustment of the inter-optical axis distance LPD may be performed automatically, e.g., before the alignment operation with respect to the examinee's eye, before objective measurement, or before subjective measurement. Alternatively, the adjustment of the inter-optical axis distance LPD may be performed based on an operation signal from the monitor 4.

The positions of the measurement optical axes L4R and L4L may be modified by modifying the positions of the measurement optical axes L4R and L4L with respect to the horizontal direction (the X-direction), using a driver (such as the driver 83) for driving the light deflecting members in the horizontal direction. With regard to a specific technique for modifying the inter-optical axis distance LPD, for example, the controller 70 may move the positions of the measurement optical axes L4R and L4L by adjusting the position of the deflecting mirrors 81R and 81L in the horizontal direction by controlling the driver 83. Of course, the deflecting mirrors 81R and 81L are not intended to be a limitation, and other light deflecting members may be used.

Figure 8A:
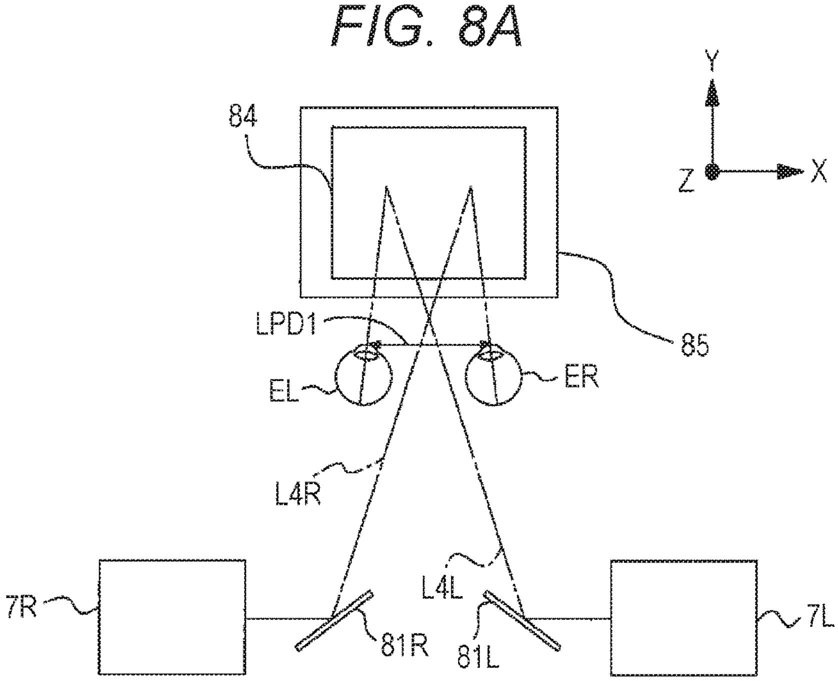
FIGS. 8A and 8B are drawings for describing modification of the distance between optical axes by a movement of deflecting mirrors.
Figure 8B:
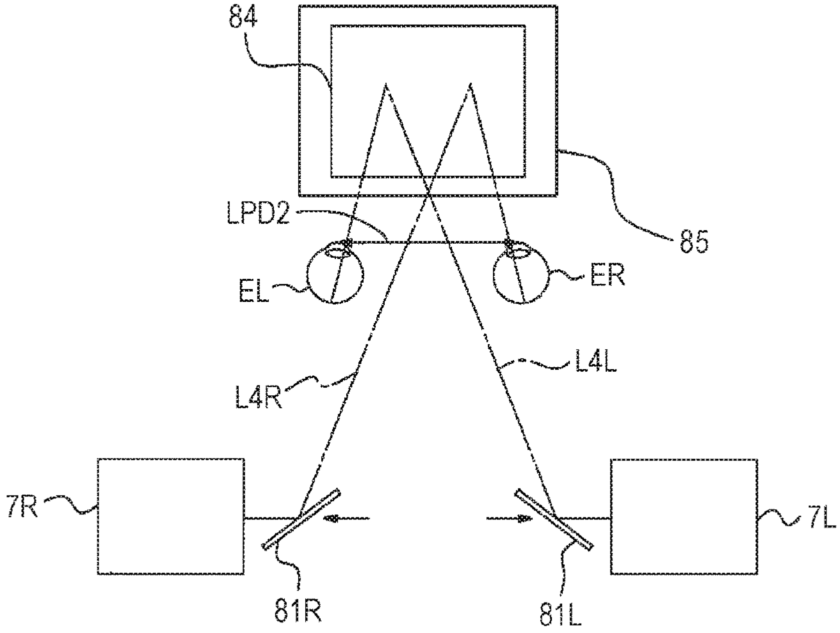

FIG. 8A and FIG. 8B are drawings for describing the modification of the inter-optical axis distance LPD through the movement of the deflecting mirror 81. In the present embodiment, the LPD can be modified by moving the deflecting mirror 81 in the X-direction. For example, referring to FIG. 8A, the deflecting mirror 81R is moved so that the distance between the right-eye measurer 7R and the deflecting mirror 81R becomes shorter (so that the deflecting mirror 81R becomes closer to the right-eye measurer 7R along the X-direction). Similarly, for example, the deflecting mirror 81L is moved so that the distance between the measurer 7L and the deflecting mirror 81L becomes shorter (so that the deflecting mirror 81L becomes closer to the measurer 7L along the X-direction). In this way, as illustrated in FIG. 8B, the deflecting mirror 81 is moved. As a result, the inter-optical axis distance LPD1 illustrated in FIG. 8A is modified to an inter-optical axis distance LPD2 illustrated in FIG. 8B.

With regard to the above-described modification of the inter-optical axis distance LPD, a correspondence relationship between the position of the light deflecting member in the horizontal direction and the interpupillary distance PD may be set in advance and stored in the memory 72. Specifically, the horizontal position of the deflecting mirrors 81R and 81L and the interpupillary distance may be associated with each other in advance. In this case, a correspondence table, a computing formula and the like may be stored in the memory 72.

For example, the controller 70 may acquire from the memory 72 the horizontal position (drive position) of the light deflecting member corresponding to the interpupillary distance of the examinee's eye obtained by the interpupillary distance measurer. The controller 70 may further cause the light deflecting member to be moved to the acquired horizontal position.

<Aberration Correction>

The controller (correction setter) 70 may set a correction amount for correcting an optical aberration caused in the optical path of the measurement optical system (such as the left-eye optical path or the right-eye optical path). The controller 70 may also correct an optical aberration caused in the optical path of the measurement optical system, by controlling the correction optical system 90 based on the set correction amount. Preferably, the aberration correction amount in the correction optical system 90 is set to an aberration amount such that the optical aberration can be cancelled. However, the aberration correction amount is not limited to such amount as long as no trouble would be posed to the examination. The aberration corrector may include the controller 70 and the correction optical system 90.

A typical example of the optical aberration caused in the optical path of the measurement optical system is astigmatism in light flux caused by the concave mirror 85. Such astigmatism may affect the subjective measurement optical system 25 and/or the objective measurement optical system 10. Astigmatism is an aberration having directionality. Correction of astigmatism may be performed so as to cancel the direction of development of astigmatism.

<Aberration Correction in Accordance with Corrective Power>

The amount of optical aberration may vary in accordance with a change in the position or area (light flux diameter) of reflection of the light flux on the concave mirror 85. For example, the area of reflection of the target light flux varies in accordance with a change in the corrective power of the corrective optical system 60. As a result, the aberration amount varies.

This means that the condensed state of light flux with respect to the concave mirror 85 differs depending on the corrective power set in the corrective optical system 60. For example, when the corrective power is 0 D, the target light flux enters the concave mirror 85 in the form of parallel light fluxes from infinity. The more the corrective power is increased on the plus side, the greater the area of reflection and aberration become because the target light flux enters the concave mirror 85 in the form of increasingly diffusive light flux. The more the corrective power is increased on the minus side, the smaller the area of reflection and therefore aberration become because the target light flux enters the concave mirror 85 in the form of increasingly convergent light flux. In accordance with such differences in the area of reflection, the amount of astigmatism introduced by the concave mirror 85 differs.

Accordingly, in the present embodiment, the amount of aberration correction by the correction optical system 90 may be changed in accordance with the corrective power of the corrective optical system 60. In this way, regardless of corrective power, a target having reduced astigmatism and decreased aberration can be presented. Accordingly, the subjective measurement or the objective measurement can be accurately performed.

In this case, a table associating corrective powers with correction amounts for correcting the astigmatism by the concave mirror 85 in accordance with the corresponding corrective powers may be created in advance. The created table may be stored in the memory 72. The correction amount for each corrective power may be determined by optical simulation or experimentally, for example. It should be noted, however, that a table may not be used. A computing formula for deriving the correction amount corresponding to each corrective power may be stored in the memory 72, and a correction amount may be determined using the computing formula.

The correction amount for each corrective power may be prepared on a spherical power by spherical power basis. In addition, in view of the difference in cylindrical power and axial angle at each spherical power, the correction amount may be prepared for each cylindrical power at each spherical power and/or for each axial angle at each spherical power. According to a simulation conducted by the present inventors, the amount of change in astigmatism is greatly influenced by a change in spherical power. By modifying the correction amount on a spherical power by spherical power basis (i.e., modifying the correction amount in accordance with a change in spherical power), a certain effect can be expected. When the correction amount is set for each corrective power, the correction amount may vary for each corrective power, or a certain correction amount may be set at predetermined steps (for example, at 1.0 D step of 0 to 1.0 D, 1.0 to 2.0, and so on). That is, the correction amount may be modified on a step by step basis.

When the corrective power of the corrective optical system 60 is set based on the objective eye refractive power (spherical power S, cylindrical power C, and astigmatic axial angle A), the controller 70 may acquire from the memory 72 an aberration correction amount in accordance with the corrective power corresponding to the objective eye refractive power (objective refractive error), and control the correction optical system 90 based on the acquired aberration correction amount.

That is, the controller 70 may set the aberration correction amount based on the objective eye refractive power obtained by the objective eye refractive power measurement apparatus (such as the objective measurement optical system 10). In addition, the controller 70 may perform aberration correction by controlling the correction optical system 90 based on the aberration correction amount set.

When the aberration correction amount is set in accordance with the corrective power, it is not necessarily required that the numerical value data of the corrective power and the aberration correction amount be associated with each other. For example, an operation signal corresponding to a corrective power that is input on the monitor 4 and an aberration correction amount may be associated with each other. Alternatively, drive information for the corrective optical system 60 (for example, the position of the display 31) and an aberration correction amount may be associated with each other. Alternatively, as described above, the result of measurement by the objective eye refractive power measurement apparatus and an aberration correction amount may be associated with each other.

When the apparent presenting distance of the target is modified, astigmatism may be caused as described above. In this case, the controller 70 modifies the aberration correction amount in accordance with the target presenting distance, thereby presenting the target with reduced aberration, regardless of the change in the presenting distance. The controller 70 may modify the aberration correction amount for the correction optical system 90 in accordance with the presenting distance of the target presented to the examinee's eye by the light projecting optical system 30. In this case, the target presenting distance and the aberration correction amount may be associated with each other. Alternatively, the drive information for the light projecting optical system 30 (such as the position of the display 31) and the aberration correction amount may be associated with each other. When the target presenting distance is modified by controlling the corrective power of the corrective optical system 60, an aberration correction amount corresponding to the corrective power incorporating the target presenting distance may be set.

The example of the aberration amount varying in accordance with a change in the area of reflection of light flux on the concave mirror 85 is not limited to the above example. When the area of reflection of the measurement light flux from the fundus that has been projected by the objective measurement optical system 10 is changed on the concave mirror 85 in accordance with a change in the eye refractive power of the examinee's eye, the aberration amount is changed. In this case, there is a possibility of distortion in the image (such as a ring image) measured by the objective measurement optical system 10. Accordingly, the aberration correction amount for the correction optical system 90 may be modified in accordance with the objective eye refractive power obtained in advance by the objective measurement optical system 10. In this way, a measured image with reduced aberration can be obtained. As a result, the eye refractive power can be accurately measured. Description of a table, a computing formula and the like for setting the aberration correction amount is omitted as a technique similar to the one for the above-described corrective power can be adopted. For the objective eye refractive power and corrective power, the same parameter (SCA) may be used. Accordingly, the same table or computing formula may be used for performing their corrections.

<Aberration Correction in Accordance with the Deflecting Angle or Position of Light Deflecting Member>

In accordance with a change in at least the deflecting angle of the light deflecting member (for example, deflecting mirrors 81R and 81L) or the horizontal position of the light deflecting member, the reflected position of the light flux (such as the target light flux or the measurement light flux of the objective measurement optical system 10) on the concave mirror 85 is changed. As a result, the aberration amount is changed.

Accordingly, in the present embodiment, the controller 70 may modify the aberration correction amount in the correction optical system 90 in accordance with at least the deflecting angle of the light deflecting member (for example, deflecting mirrors 81R and 81L) or the horizontal position of the light deflecting member. In this way, a satisfactory target with decreased astigmatism can be presented regardless of the deflecting angle and horizontal position of the light deflecting member. In addition, a satisfactory measured image with decreased astigmatism can be acquired regardless of the deflecting angle and horizontal position of the light deflecting member. Accordingly, the subjective measurement or objective measurement can be accurately performed.

In this case, a table may be created in which the correction amount for correcting the astigmatism due to the concave mirror 85 is set in advance for each parameter (deflecting angle and horizontal position). The created table may be stored in the memory 72. The correction amount may be determined by optical simulation or experimentally, for example. The table, however, is not a requirement; a computing formula for deriving the aberration correction amount may be stored in the memory 72, and a correction amount may be determined according to the computing formula. In this case, the correction amount may vary depending on the parameter, or a certain correction amount may be set in predetermined steps of the parameter. That is, the correction amount may be changed on a step by step basis.

When the aberration correction amount is set in accordance with the deflecting angle of the light deflecting member, it is not necessarily required that numerical value data of deflecting angle and the aberration correction amount be associated with each other. The drive angle information of the light deflecting member (for example, a drive signal for the driver 82) and the aberration correction amount may be associated with each other. In addition, as described above, when the convergence angle of the target light flux is modified in accordance with the target presenting distance, the convergence angle and the aberration correction amount may be associated with each other. That is, the controller 70 may modify the aberration correction amount for the correction optical system 90 in accordance with the convergence angle of the target light flux modified by the driving of the light deflecting member. In addition, as described above, when the position of the measurement optical axes L1R and L1L (alignment position) with respect to the examinee's eye is adjusted by adjusting the deflecting angle of the light deflecting member, the alignment position of the examinee's eye and the aberration correction amount may be associated with each other.

When the aberration correction amount is set in accordance with the position of the light deflecting member, it is not necessarily required that the position data and the aberration correction amount be associated with each other. The drive position information of the light deflecting member (for example, a drive signal for the driver 82) and the aberration correction amount may be associated with each other. In addition, as described above, when the pair of measurement optical systems is associated with the interpupillary distance by adjusting the horizontal position of the light deflecting member, the interpupillary distance and the aberration correction amount may be associated with each other. That is, the controller 70 may modify the aberration correction amount for the correction optical system 90 in accordance with the interpupillary distance of the examinee's eye.

<Handling of a Plurality of Parameters>

The above-described aberration correction in accordance with corrective power may be implemented simultaneously with the aberration correction in accordance with the deflecting angle or position of the light deflecting member at the time of subjective measurement. In this case, an aberration correction amount may be set by acquiring the aberration correction amounts individually, and then summing them. The aberration correction amount in accordance with corrective power varies in accordance with a change in the deflecting angle and position of the light deflecting member. Accordingly, more preferably, a table, a computing formula and the like for deriving the most appropriate aberration correction amount from the three parameters of corrective power, the deflecting angle of the light deflecting member, and the position of the light deflecting member may be stored in the memory 72 in advance. In this case, the aberration correction amount for the correction optical system 90 may be modified in accordance with a change in at least one of the parameters.

In other words, when the aberration correction amount is determined based on a plurality of parameters, a table, a computing formula and the like for deriving the most appropriate aberration correction amount from a plurality of parameters may be stored in the memory 72 in advance. Similarly, for example, the aberration correction in accordance with the objective eye refractive power may be implemented simultaneously with the aberration correction in accordance with the deflecting angle or position of the light deflecting member at the time of objective measurement. In this case, the aberration correction amount may be set by acquiring aberration correction amounts individually, and then summing them. The aberration correction amount in accordance with the objective eye refractive power varies in accordance with a change in the deflecting angle and position of the light deflecting member. Accordingly, more preferably, a table, a computing formula and the like for deriving the most appropriate aberration correction amount from the three parameters of the objective eye refractive power, the deflecting angle of the light deflecting member, and the position of the light deflecting member may be stored in the memory 72 in advance. In this case, the aberration correction amount for the correction optical system 90 may be modified in accordance with a change in at least one of the parameters.

<Control Operation>

In the following, a control operation by the subjective optometry apparatus 1 will be described. The examiner instructs the examinee to rest his or her jaw on the chin rest 5 and observe the presentation window 3. The examiner then instructs the examinee to fixate on the fixation target displayed on the display 31. Thereafter, alignment of the examinee's eye (adjustment of the position of the examinee's eye) is performed. When the alignment start switch is selected by the examiner, the controller 70 starts automatic alignment.

For example, the controller 70 detects the position of the pupil of the examinee's right and left eyes from a facial image captured by means of the imaging optical system 100. When the pupil position is detected, the controller 70 controls the subjective optometry apparatus 1 so that an anterior segment image is displayed on the monitor 4, for example. The controller 70 drives the right-eye deflecting mirror 81R and the left-eye deflecting mirror 81L respectively to rotate in the X- and Y-directions, for example. When the pupil position is detected, the controller 70 may cause the right-eye measurer 7R and the left-eye measurer 7L respectively to be moved in the X-direction, for example. That is, the controller 70 performs alignment in the X- and Y-directions by driving the deflecting mirror 81, and performs alignment in the Z-direction by driving the measurer 7.

In the present embodiment, by way of example, the alignment in the X-, Y-, and Z-directions is implemented by driving the deflecting mirror 81 and the measurer 7. However, this is not a limitation, and the embodiment of the present disclosure need only to be configured so that the positional relationship between the examinee's eye and the subjective and objective measurer can be adjusted. That is, the embodiment of the present disclosure need only to be configured to be able to implement the alignment in the X-, Y-, and Z-directions so that an image corrected by the corrective optical system 60 can be formed on the fundus of the examinee's eye. For example, the chin rest 5 may be fitted with a member capable of moving the subjective optometry apparatus 1 in the X-, Y-, and Z-directions, whereby the subjective optometry apparatus 1 can be moved for alignment. The alignment in the X-, Y-, and Z-directions may be performed only by means of the deflecting mirror 81, for example. In this case, a member for moving the deflecting mirror 81 in the Z-direction may be provided so as to modify the distance between the deflecting mirror 81 and the measuring unit as well as rotationally driving the deflecting mirror 81.

Figure 9:
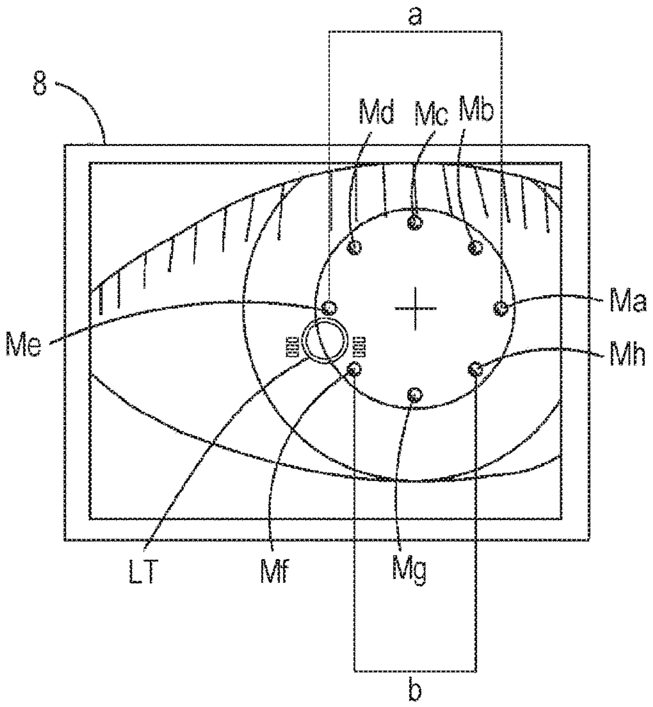
FIG. 9 illustrates an anterior segment observation screen with an anterior segment image captured by an imaging device displayed therein.

FIG. 9 illustrates an anterior segment observation screen in which an anterior segment image captured by the two-dimensional imaging device 52 is displayed. In the present embodiment, alignment control with respect to one of the examinee's eyes will be described. The control that will be described below is similarly performed for the other of the examinee's eyes. During the alignment control, the examinee's both eyes may be displayed on the monitor 4, and the alignment control for both of the examinee's eyes may be performed on the same screen. During the alignment control, one of the examinee's eyes may be displayed on the monitor 4, and, after the alignment control for one of the eyes of the examinee is completed, the other of the examinee's eyes may be displayed on the monitor 4, and then the alignment control for the other of the examinee's eyes may be performed. The alignment control for the other of the examinee's eyes may be performed based on the result of the alignment control for one of the examinee's eyes, for example.

The controller (displacement detector, corrector) 70 detects, e.g., displacement of an image of the corrective optical system 60 with respect to the examinee's eye. For example, the controller 70, by controlling the driver based on a detection result, deflects an apparent light flux for guiding the image of the corrective optical system 60 to the examinee's eye. In this way, the controller 70 optically corrects the formation position of the image. Thus, in the subjective optometry apparatus 1 according to the present embodiment, the controller 70 detects a displacement between the examinee's eye and the corrective optical system, and optically corrects the formation position of the image. By thus correcting the displacement between the examinee's eye and the corrective optical system, the apparatus can be used with the examinee's eye located at an appropriate position. Accordingly, an accurate measurement can be taken.

More specifically, for example, during alignment, the light sources for the first target projecting optical system 45 and the second target projecting optical system 46 are turned on. The controller 70 detects the X and Y center coordinates (see the cross mark in FIG. 9) of the target images Ma to Mh projected in ring shape, as a substantial corneal apex position Mo, for example. In order to determine the alignment state, an alignment reference position O1 in the X- and Y-directions is set, for example. In the present embodiment, the alignment reference position O1 is set, e.g., as the position at which the corneal apex position and the optical axis of the subjective optometry apparatus 1 (the optical axis of the optical path along which the light flux reflected by the concave mirror 85 passes) L4 (L4R, L4L) coincide with each other. For example, the alignment reference position O1 is an alignment reference position used by the subjective optometry apparatus 1. In a predetermined region with the alignment reference position O1 disposed at the center, an alignment allowable range A1 for determining the appropriateness of alignment is set, for example.

Figure 10:
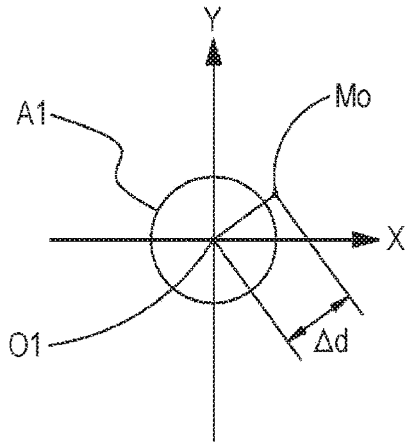
FIG. 10 is a drawing for describing alignment control.

FIG. 10 is a drawing for describing alignment control. For example, the controller 70 determines the amount of alignment deviation Δd between the alignment reference position O1 and the corneal apex position Mo. The controller 70 implements alignment in the X- and Y-directions by driving the deflecting mirror 81 so that the amount of alignment deviation Δd enters the alignment allowable range A1.

The controller 70 also determines the amount of alignment deviation Δd in the Z-direction by determining (comparing) an image ratio (a/b) of an image interval a of infinity target images Ma and Me, and an image interval b of finite-distance target images Mh and Mf. If there is displacement in the operation distance between the examinee's eye and the subjective optometry apparatus 1 (distance in the Z-direction), the above-described interval of the infinity targets Ma and Me hardly changes whereas the image interval of the target images Mh and Mf is changed. The controller 70, using the property, determines the amount of alignment deviation in the operation distance direction with respect to the examinee's eye (see JP-A-6-46999 for greater detail).

The controller 70 also determines the amount of alignment deviation Δd with respect to the alignment reference position in the Z-direction, as in the X- and Y-directions. The controller 70 implements the alignment in the Z-direction by controlling the driving of the measurer 7 so that the amount of alignment deviation Δd enters the alignment allowable range A1 for the Z-direction.

In this case, the controller 70 stops the driving of the deflecting mirror 81 and the measurer 7, and outputs an alignment completion signal when the amount of alignment deviation Δd in the X-, Y-, and Z-directions has entered the alignment allowable range A1. Even after the completion of alignment, the controller 70 detects the amount of alignment deviation Δd as needed. The controller 70, when the amount of alignment deviation Δd has exceeded the alignment allowable range A1, resumes the automatic alignment. That is, the controller 70 performs control (tracking) to cause the photography units (deflecting mirror 81 and measurer 7) to track the eye E so that the amount of alignment deviation Δd satisfies the alignment allowable range A1.

In the present embodiment, the controller 70 performs alignment control automatically by way of example. However, the alignment method is not limited to such example. In another example, the controller 70 may implement alignment as follows. That is, the controller 70 displays, on the monitor 4, a mark electronically indicating the alignment reference position. The examiner adjusts the positional relationship between the alignment reference position and the examinee's eye by operating the monitor 4. In this case, when the alignment in the X-, Y-, and Z-directions is complete, the controller 70 may cause the monitor 4 to display an indication to that effect.

The examiner may guide the examinee until proper alignment state is achieved (until alignment is complete), for example. In this case, when the corneal apex position has entered the alignment allowable range, the controller 70, determining that the alignment in the X-, Y-, and Z-directions is complete, may cause the monitor 4 to display an indication to that effect.

<Objective Measurement>

Based on the output of an alignment completion signal, the controller 70 emits a trigger signal for starting the objective measurement. After emitting the trigger signal for starting the objective measurement, the controller 70 causes the objective measurement optical system 10 to emit a measurement light flux. In this case, each of the measurement light fluxes is reflected by the concave mirror 85 via the deflecting mirrors 81R and 81L, and projected onto the fundus of the examinee's eye. The measurement light reflected by the fundus is reflected by the deflecting mirror 81R (81L) via the concave mirror 85. Thereafter, the measurement light flux is received by the imaging device 22, which then captures a measured image.

For example, during the measurement of objective eye refractive power, a preliminary measurement for the eye refractive power may be initially performed. Based on the result of the preliminary measurement, the display 31 may be moved in the optical axis L2 direction, so as to fog the examinee's eye E. That is, the display 31 may be once moved to the position of focus with respect to the examinee's eye E, and then a main measurement for the eye refractive power may be performed with respect to the fogged examinee's eye. During the main measurement, a measured image is captured by the imaging device 22. An output signal from the imaging device 22 is stored in the memory 72 as image data (measured image). Thereafter, the controller 70 subjects a ring image stored in the memory 72 to image analysis to determine the values of refractive powers in the meridian directions. The controller 70 then subjects the refractive power to a predetermined process to thereby obtain the objective eye refractive power (objective values) for distance vision, including the spherical power (S), cylindrical power (C), and astigmatic axial angle (A) of the examinee's eye. The obtained objective values for distance vision are stored in the memory 72.

During the measurement of the objective eye refractive power, the controller 70 may also control the correction optical system 90 so as to correct optical aberration caused in the optical path of the objective measurement optical system 10. In this case, the controller 70 acquires from the memory 72 a correction amount corresponding to the dioptric power measured by the objective measurement optical system 10. The controller 70 then controls the correction optical system 90 based on the acquired aberration correction amount.

More specifically, in accordance with the eye refractive power obtained by the preliminary measurement, a correction amount is set. Based on the correction amount set, the correction optical system 90 is driven. In this way, the main measurement is performed with the aberration caused in the optical path of the objective measurement optical system 10 having been corrected. Accordingly, the objective eye refractive power can be accurately measured. When the eye refractive power is to be successively measured (for example, when the main measurement is performed multiple times), the correction optical system 90 may be controlled based on the result of each measurement.

In the foregoing description, the objective eye refractive power for distance vision is measured. However, this is not a limitation. For example, the objective eye refractive power for near vision, which is the eye refractive power in a state of target presentation at a short distance, may be measured. The objective eye refractive power for the right and left eyes may be measured simultaneously or at different timings.

<Subjective Measurement>

When the objective refractive power measurement is complete and the monitor (which, in the present embodiment, also serves as an operating unit) 4 is operated, the measurement mode is switched to the subjective visual acuity measurement mode for distance vision (subjective refractive power measurement mode). The controller 70 may correct the refractive error of the examinee's eye by driving the corrective optical system 60, based on the objective eye refractive power of the examinee's eye (spherical power S, cylindrical power C, and astigmatic axial angle A) that has been obtained by the objective refractive power measurement for distance vision.

More specifically, the display 31 may be moved in the optical axis L2 direction based on the spherical power S at the time of the objective refractive power measurement for distance vision. As a result, a state in which the refractive error regarding the spherical power of the examinee's eye is corrected can be obtained. In addition, based on the cylindrical power C and the astigmatic axial angle A, the astigmatism corrective optical system 63 may be driven. As a result, a state in which the refractive power error regarding the astigmatism of the examinee's eye is corrected can be obtained.

In the visual acuity measurement mode, the controller (correction setter) 70 may modify the amount of aberration correction by the correction optical system 90 in accordance with the corrective power corrected by the corrective optical system 60. For example, when the corrective power of the corrective optical system 60 is modified based on an operation signal from the monitor 4, the controller 70 may modify the amount of aberration correction by the correction optical system 90, in accordance with the modified corrective power. In this way, even when the corrective power is modified based on the result of measurement by an auto refractometer, a target with reduced aberration is presented. That is, the controller 70 may set the correction amount for correcting the optical aberration caused in the subjective measurer, based on the corrective power of the corrective optical system 60.

The controller 70 may also control the display 31 to display a target of a required visual acuity value (for example, a target with visual acuity value of 0.8) on the optical axis L2. When the initial presentation target is presented to the examinee's eye, the examiner performs distance visual acuity measurement on the examinee. The visual acuity value target that is presented may be switched by pressing a predetermined switch on the monitor 4.

For example, if the examinee's response is correct, the examiner switches the presented target to a target having a visual acuity value that is higher by one step. On the other hand, if the examinee's response is wrong, the presented target is switched to a target having a visual acuity value that is lower by one step. That is, the controller 70 may switch the presented target on the basis of a visual acuity value modification signal from the monitor 4.

The examiner, by modifying the corrective power of the corrective optical system 60 using the monitor 4, may also determine the subjective eye refractive power of the examinee's eye with the target presented at a far distance (distance subjective values including spherical power S, cylindrical power C, and astigmatic axial angle A).

The corrective power of the corrective optical system 60 may be set to different powers for the right and left eyes, or to the same power for the right and left eyes. The subjective eye refractive power for the right and left eyes may be measured simultaneously or at separate timings. When the subjective eye refractive power for the right and left eyes are measured at separate timings, the display 31 may not display the target to the eye that is not being measured. Alternatively, with respect to the eye that is not being measured, fogging may be performed by the corrective optical system 60 (whereby, for example, a certain dioptric power is added to an objective value).

After the distance subjective value is determined, the measurement mode may be switched to the subjective near visual acuity measurement mode. When the measurement mode is set to the near measurement mode, the controller 70 may cause a target to be presented at a near position by controlling the light projecting optical system 30 and thereby modifying the convergence angle by the deflecting mirror 81. The target presenting distance during near examination may be arbitrarily modified based on an operation signal from the monitor 4. As a result, the target presenting distance may be modified from far position to near position. During near examination, addition and accommodation ability may be subjectively determined by modifying the target presenting distance (near position).

In this case, for example, the controller 70 may acquire from the memory 72 an aberration correction amount in accordance with the target presenting distance, and control the correction optical system 90 based on the acquired aberration correction amount. When the target presenting distance is modified, the controller 70 may modify the amount of aberration correction by the correction optical system 90 in accordance with the modified target presenting distance. In this way, when the target presenting distance is modified, a target with reduced aberration is presented. In this case, the controller 70 may modify the aberration correction amount in accordance with the corrective power to which the target presenting distance is added.

Further, the controller 70 may modify the convergence angle of the right and left target light fluxes by controlling the light deflecting member in accordance with the modification of the target presentation position. In this case, for example, the controller 70 may acquire from the memory 72 an aberration correction amount in accordance with the deflecting angle of the light deflecting member corresponding to the convergence angle. The controller 70, based on the acquired aberration correction amount, may control the correction optical system 90. When the convergence angle of the target light flux is modified, the controller 70 may modify the amount of aberration correction by the correction optical system 90 in accordance with the modified convergence angle. In this way, when the convergence angle is modified, a target with reduced aberration is presented.

During the near examination, as in the distance examination, the examiner may modify the corrective power of the corrective optical system 60 using a predetermined switch of the monitor 4, and measure the subjective eye refractive power (near subjective value) with the target presented at a short distance. During the near examination, the controller 70 may modify the aberration correction amount for the correction optical system 90 in accordance with the modification of the corrective power.

As described above, during the objective examination and subjective examination, the examinations as a whole can be performed in a satisfactory manner by modifying the aberration correction amount. In the foregoing description, aberration correction is performed for both objective examination and subjective examination. However, this is not a limitation, and the modification of the aberration amount by the correction optical system 90 may be performed for either objective examination or subjective examination.

In the foregoing description, the correction optical system 90 is provided separately from the corrective optical system 60. However, the embodiment can also be applied when the corrective optical system 60 also serves as the correction optical system 90. For example, as the correction optical system 90, the astigmatism corrective optical system (astigmatism correction optical system) 63 may be used. In this case, for example, an aberration correction amount may be added to the cylindrical power and axial angle as the corrective power. That is, the controller 70 (aberration corrector) may also correct the optical aberration caused in the subjective measurer, using the corrective optical system 60.

In the above configuration, the optical systems are designed such that the optical axis of the measurement optical system is disposed on the optical axis of the concave mirror 85. Accordingly, aberration generated by the concave mirror 85 can be suppressed. Accordingly, the amount of aberration correction by the correction optical system 90 can be decreased. It should be noted, however, that the present embodiment can also be applied in a configuration in which the optical axis of the measurement optical system is disposed outside the axis of the concave mirror 85.

<Auxiliary Optical Member>

In case the examinee's eye has severe refractive error, the subjective measurement optical system 25 may be configured such that an auxiliary optical member can be disposed on the optical path of the subjective measurement optical system. The auxiliary optical member may be a lens, a prism, or a mirror, for example. If the diopter value of the examinee's eye that is measured is large, it may not be possible to correct the optical aberration with the correction optical system 90 alone. The auxiliary optical member may be used to correct such optical aberration that cannot be corrected with the correction optical system 90 alone, whereby accurate measurement can be performed. More specifically, when the diopter value of the examinee's eye is 13.0 D, for example, the examinee is asked to wear the auxiliary optical member (such as a trial frame) for 10.0 D. The controller 70 then performs measurement in that state, and corrects the acquired measurement result in light of the corrective power of the auxiliary optical member. For example, when the measurement result is 3.0 D, the controller 70 corrects the measurement result and outputs a result indicating that the examinee's diopter value is 13.0 D.

In this case, the controller (determiner) 70 may perform a determination process for determining whether, based on the eye refractive power acquired by the objective measurer, the auxiliary optical member is required or not. In addition, the controller (insertion/removal unit) 70 may perform an insertion/removal control for the auxiliary optical member into and out of the optical path of the subjective measurement optical system 25, based on the result of the determination process. In this way, insertion and removal of the auxiliary optical member is automatically performed, whereby the measurement can be easily and accurately performed. The auxiliary optical member is particularly useful for small-sized apparatus, such as the subjective optometry apparatus 1 according to the present embodiment. When the distance from the concave mirror 85 to the examinee's eye is small, for example, the change in the aberration amount by the corrective power tends to be increased. Accordingly, the auxiliary optical member may be used to correct optical aberration that cannot be corrected by means of the correction optical system 90 alone.

This is not intended to be a limitation, and the controller (display unit) 70 may cause the monitor 75 to display notification information based on the result of the determination process. The subjective measurement optical system 25 may be configured such that, when the notification information indicating that the auxiliary optical member is required is displayed, the examiner can dispose the auxiliary optical member on the optical path. In this case, an auxiliary lens may be worn by the examinee. In this case, the examiner can be notified of the need for the auxiliary optical member. Accordingly, the examiner can easily recognize the need for the auxiliary optical member. In this way, the examiner can be prevented from forgetting to use the auxiliary optical member.

In the above configuration, the optical aberration caused in the optical path of the measurement optical system is optically corrected by the correction optical system 90. However, this is not a limitation and other correction processes may be performed. For example, aberration in an image measured by the objective measurement optical system 10 may be corrected in accordance with the optical aberration caused in the optical path of the measurement optical system. In addition, an objective value by the objective measurement optical system 10 may be corrected in accordance with the optical aberration caused in the optical path of the measurement optical system.

The technology relating to aberration correction in the present embodiment is applicable to a subjective optometry apparatus without an objective measurer. The technology relating to aberration correction in the present embodiment is also applicable, for example, to a subjective optometry apparatus that does not have a corrective optical system including a right-left pair of an examinee's right-eye corrective optical system and an examinee's left-eye corrective optical system, nor the concave mirror 85 shared by a right-eye optical path including the right-eye corrective optical system and a left-eye optical path including the left-eye corrective optical system. That is, the technology relating to aberration correction in the present embodiment is applicable to a subjective optometry apparatus provided with a subjective measurer for subjectively measuring the optical characteristics of the examinee's eye. The subjective optometry unit includes: a light projecting optical system for projecting a target light flux toward an examinee's eye; a corrective optical system which is disposed on an optical path of the light projecting optical system and which modifies an optical characteristic of the target light flux; and an optical member which guides the target light flux corrected by the corrective optical system to the examinee's eye, and which forms an image of the target light flux corrected by the corrective optical system in front of the examinee's eye. The subjective optometry apparatus may be provided with: a correction setter for setting a correction amount for correcting optical aberration caused in the subjective measurer, based on a corrective power of the corrective optical system; and an aberration corrector for correcting the optical aberration caused in the subjective measurer, on the basis of the correction amount set by the correction setter.

<Modification of Alignment Allowable Range>

The controller 70 may set an alignment allowable range for performing alignment state determination based on eye refractive power. For example, the controller 70, based on the objective eye refractive power of the examinee's eye (spherical power S, cylindrical power C, and astigmatic axial angle A) obtained by objective refractive power measurement for distance vision, sets an alignment allowable range for determining alignment state between the examinee's eye and the subjective measurer at the time of subjective eye refractive power measurement. That is, for example, the controller (acquisitor, setter (alignment setter)) 70 may acquire the eye refractive power of the examinee's eye E that has been objectively measured. In addition, the controller 70 may set the alignment allowable range for determining the alignment state between the examinee's eye E and the subjective measurer, based on the eye refractive power. In the following, the setting of alignment allowable ranges in the X- and Y-directions will be described. An alignment allowable range in the Z-direction is similarly set.

In the present embodiment, by way of example, a configuration will be described in which, using the objective eye refractive power of the examinee's eye that has been acquired by the objective measurer of the subjective optometry apparatus 1, the alignment allowable range is modified. The configuration for modifying the alignment allowable range, however, is not limited to the configuration of the present embodiment. For example, a configuration for modifying the alignment allowable range may employ a measurement result acquired by a different objective measurement apparatus and received therefrom.

More specifically, for example, in the present embodiment, the alignment allowable range is prepared for each spherical power. Of course, the alignment allowable range may be set based on the eye refractive power. For example, the alignment allowable range may be created for each cylindrical power and each axial angle at each spherical power, in light of the differences in the cylindrical power and axial angle at the spherical power.

Figure 11A:
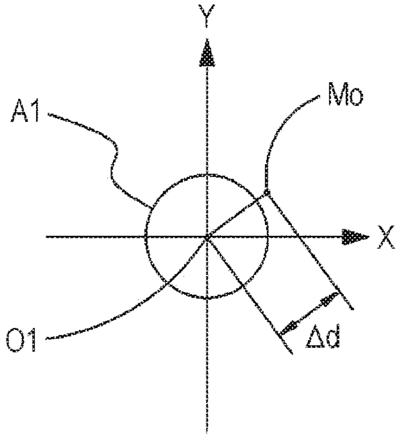
FIGS. 11A to 11C are drawings for describing modification of an alignment allowable range.
Figure 11B:
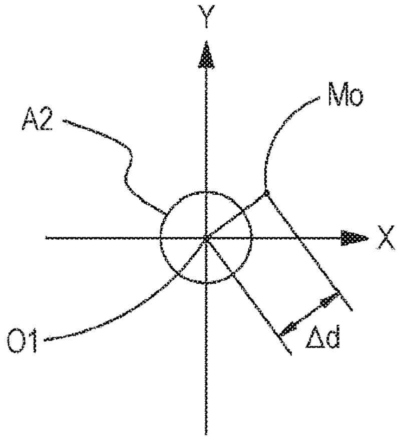
Figure 11C:
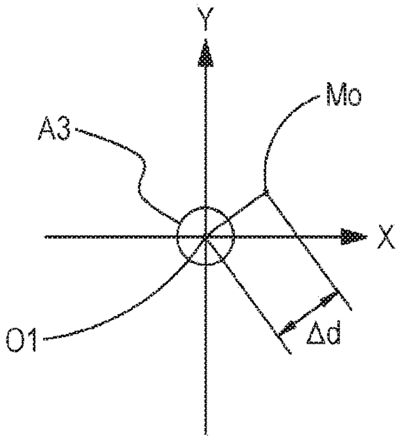

FIGS. 11A to 11C are drawings for describing a modification of the alignment allowable range. FIG. 11A illustrates an alignment allowable range in a case where the diopter value (D) is 0 D. FIG. 11B illustrates an alignment allowable range in a case where the diopter value is 2.0 D. FIG. 11C illustrates an alignment allowable range in a case where the diopter value is 5.0 D. The alignment allowable range is set according to the eye refractive power, for example. The alignment allowable range may be calculated by simulation or experiment and set in advance. Of course, the alignment allowable range may be calculated and set according to the eye refractive power before and after alignment control.

For example, the controller 70 is configured to decrease the alignment allowable range as the diopter value increases in the plus direction (plus side) or minus direction (minus side) from 0 D, with reference to zero diopter (0 D). For example, the alignment allowable range A2 illustrated in FIG. 11B, which is for the case where the diopter value is 2.0 D, is set to be smaller than the alignment allowable range A1 illustrated in FIG. 11A, which is for the diopter value of 0 D. The alignment allowable range A3 illustrated in FIG. 11C, which is for the diopter value of 5.0 D, is set to be even smaller than the alignment allowable range A2 of FIG. 11B for the diopter value of 2.0 D.

For example, with regard to an examinee's eye having predetermined optical characteristics, if the alignment allowable range is set to be greater than an appropriate alignment range for acquiring an accurate measurement result, the accuracy of the measurement result when the optical characteristics of the examinee's eye are subjectively measured is decreased. In addition, with regard to the examinee's eye having the predetermined optical characteristics, if the alignment allowable range is set to be smaller than the appropriate alignment range for acquiring an accurate measurement result, alignment operation becomes difficult when the optical characteristics of the examinee's eye are subjectively measured. The subjective optometry apparatus 1 according to the present embodiment is configured to modify the alignment allowable range based on the eye refractive power. In this way, when the optical characteristics of the examinee's eye are subjectively measured, the optical characteristics of the examinee's eye can be accurately measured. In addition, when the optical characteristics of the examinee's eye are subjectively measured, an efficient alignment operation can be performed, for example.

For example, the subjective optometry apparatus 1 according to the present embodiment is configured to decrease the alignment allowable range when the diopter value is increased in the plus direction or minus direction from zero diopter, with reference to zero diopter. In this way, a decrease in the accuracy of the measurement result when the optical characteristics of the examinee's eye are subjectively measured can be limited. In addition, when, with reference to zero diopter, the diopter value is close to zero diopter, the alignment allowable range is increased. In this way, when the optical characteristics of the examinee's eye are subjectively measured, the alignment operation can be prevented from becoming difficult.

The subjective optometry apparatus 1 according to the present embodiment is provided with the corrective optical system 60. The corrective optical system 60 includes the right-left pair of the examinee's right-eye corrective optical system and the examinee's left-eye corrective optical system, and is disposed on the optical path of the light projecting optical system 30 to modify an optical characteristic of the target light flux. The subjective optometry apparatus 1 according to the present embodiment is also provided with the subjective measurer including the concave mirror 85 shared by the right-eye optical path having the right-eye corrective unit and the left-eye optical path having the left-eye corrective unit. The concave mirror 85 guides the target light flux that has passed through the corrective optical system 60 to the examinee's eye, and forms, in front of the examinee's eye, an image of the target light flux that has passed through the corrective optical system 60.

In the subjective optometry apparatus according to the present embodiment, it is particularly useful to modify the alignment allowable range based on the eye refractive power. For example, according to typical subjective measurer, a corrective optical system is disposed in front of the examinee's eye. When a subjective measurement is performed, the examinee gazes into the examination window of the corrective optical system. Because the examinee gazes into the examination window, the position of the examinee's eye is not greatly displaced. Accordingly, the optical characteristics of the examinee's eye can be subjectively and accurately measured. On the other hand, the subjective measurer of the subjective optometry apparatus 1 according to the present embodiment measures the refractive power of the examinee's eye without placing the corrective optical system in front of the eye. In such apparatus, the position of the examinee's eye could be greatly displaced, and therefore an alignment operation is implemented. Accordingly, in the subjective measurer that measures the refractive power of the examinee's eye without placing the corrective optical system around the eye, particularly, it is preferable to perform the alignment operation efficiently when the optical characteristics of the examinee's eye are subjectively measured. In addition, in the subjective optometry apparatus provided with the subjective measurer which measures the refractive power of the examinee's eye without placing the corrective optical system in front of the eye, particularly, it is preferable to implement the setting of the alignment allowable range so that the optical characteristics of the examinee's eye can be accurately measured when the optical characteristics of the examinee's eye are subjectively measured.

The subjective optometry apparatus 1 according to the present embodiment is provided with the objective measurer including the objective measurement optical system 10. The objective measurement optical system 10 emits measurement light toward the fundus of the examinee's eye, and receives reflected light thereof. The objective measurer objectively measures the optical characteristics of the examinee's eye. Accordingly, in the subjective optometry apparatus 1 according to the present embodiment, the controller 70 can acquire the eye refractive power based on a result of measurement by the objective measurer. Accordingly, the alignment allowable range can be modified by a single apparatus. In this way, the subjective optometry apparatus 1 according to the present embodiment, using a simple configuration, can accurately measure the optical characteristics of the examinee's eye when the optical characteristics of the examinee's eye are subjectively measured. In addition, the subjective optometry apparatus 1 according to the present embodiment, using a simple configuration, can efficiently perform an alignment operation when the optical characteristics of the examinee's eye are subjectively measured.

The technology relating to the modification of the alignment allowable range according to the present embodiment is also applicable to a subjective optometry apparatus that does not have an objective measurer. The technology relating to the modification of the alignment allowable range according to the present embodiment is also applicable to, e.g., a subjective optometry apparatus that does not include a corrective optical system including a right-left pair of examinee's right-eye corrective optical system and examinee's left-eye corrective optical system, and/or the concave mirror 85. That is, the technology relating to the modification of the alignment allowable range according to the present embodiment is applicable to the following subjective optometry apparatus. The subjective optometry apparatus is provided with a subjective measurer. The subjective measurer includes: a light projecting optical system for projecting a target light flux toward an examinee's eye; and a corrective optical system which is disposed on an optical path of the light projecting optical system and which modifies an optical characteristic of the target light flux, the subjective measurer subjectively measuring the optical characteristic of the examinee's eye. The subjective optometry apparatus may be further provided with: an acquisitor for acquiring the eye refractive power of the examinee's eye that has been objectively measured; and a setter for setting an alignment allowable range for determining an alignment state between the examinee's eye and the subjective measurer, based on the eye refractive power.

The mode of carrying out the present disclosure is not limited to the apparatus described in the present embodiment. For example, subjective optometry software (program) for implementing the functionality of the embodiment may be supplied via a network or various storage media and the like to a system or apparatus. In addition, a control apparatus (such as a CPU) of the system or apparatus may be configured to read and execute the program.

The embodiments of the present disclosure may include the following first to sixteenth subjective optometry apparatuses, and first subjective optometry program.

The first subjective optometry apparatus includes: a subjective measurer including a light projecting optical system for projecting a target light flux toward an examinee's eye, a corrective optical system including a right-left pair of a right-eye corrective optical system and a left-eye corrective optical system, and disposed on an optical path of the light projecting optical system to change an optical characteristic of the target light flux, and an optical member shared by a right-eye optical path including the right-eye corrective optical system and a left-eye optical path including the left-eye corrective optical system, the optical member for guiding the target light flux corrected by the corrective optical system to the examinee's eye, the subjective measurer subjectively measuring the optical characteristic of the examinee's eye; and an objective measurer including a measurement optical system that emits measurement light toward the fundus of the examinee's eye and that receives reflected light thereof, the objective measurer objectively measuring the optical characteristic of the examinee's eye via the optical member disposed on an optical path of the measurement optical system.

The second subjective optometry apparatus is the first subjective optometry apparatus wherein an optical axis between the optical member and the examinee's eye in the subjective measurer, and an optical axis between the optical member and the examinee's eye in the objective measurer are coaxial.

The third subjective optometry apparatus is the first or second subjective optometry apparatus wherein the optical member is a concave mirror, and the subjective measurer is configured to guide the target light flux to the examinee's eye by reflecting, using the concave mirror, the target light flux corrected by the corrective optical system toward the examinee's eye, so as to guide an image of the target light flux corrected by the corrective optical system to the examinee's eye while achieving an optically predetermined examination distance.

The fourth subjective optometry apparatus is any one of the first to third subjective optometry apparatuses, further including: a displacement detector for detecting displacement of an image of the corrective optical system with respect to the examinee's eye; a right-left pair of deflecting members disposed between the corrective optical system and the examinee's eye; a driver for driving the deflecting member; and a corrector for controlling the driver based on a result of detection by the displacement detector, and for optically correcting a formation position of the image, by deflecting an apparent light flux for guiding the image of the corrective optical system to the examinee's eye.

The fifth subjective optometry apparatus includes a subjective measurer including a light projecting optical system for projecting a target light flux toward an examinee's eye, a corrective optical system disposed on an optical path of the light projecting optical system to change an optical characteristic of the target light flux, and an optical member for guiding the target light flux corrected by the corrective optical system to the examinee's eye, the subjective measurer subjectively measuring the optical characteristic of the examinee's eye, the subjective optometry apparatus further including a correction setter for setting a correction amount for correcting optical aberration caused in the subjective measurer, based on a corrective power of the corrective optical system, and a corrector for correcting the optical aberration caused in the subjective measurer, based on the correction amount set by the correction setter.

The sixth subjective optometry apparatus includes a subjective measurer including a light projecting optical system for projecting a target light flux toward an examinee's eye, a corrective optical system disposed on an optical path of the light projecting optical system to change an optical characteristic of the target light flux, and an optical member for guiding the target light flux corrected by the corrective optical system to the examinee's eye, the subjective measurer subjectively measuring the optical characteristic of the examinee's eye, the subjective optometry apparatus further including: a controller for modifying a formation position of an image of the target light flux, and modifying a distance of target presentation by the target light flux; a correction setter for setting a correction amount for correcting optical aberration caused in the subjective measurer, based on the presentation distance; and a corrector for correcting the optical aberration caused in the subjective measurer, based on the correction amount set by the correction setter.

The seventh subjective optometry apparatus includes: a subjective measurer including a light projecting optical system for projecting a target light flux toward an examinee's eye, a corrective optical system disposed on an optical path of the light projecting optical system to change an optical characteristic of the target light flux, and an optical member for guiding the target light flux corrected by the corrective optical system to the examinee's eye, the subjective measurer subjectively measuring the optical characteristic of the examinee's eye, the subjective optometry apparatus further including: a convergence angle modifier for modifying a convergence angle of the target light flux emitted from the right-eye optical path and the left-eye optical path; a correction setter for setting a correction amount for correcting optical aberration caused in the subjective measurer, based on the convergence angle; and a corrector for correcting the optical aberration caused in the subjective measurer, based on the correction amount set by the correction setter.

The eighth subjective optometry apparatus is any one of the fifth to seventh subjective optometry apparatuses, wherein the corrective optical system also serves as the corrector.

The ninth subjective optometry apparatus is the fifth subjective optometry apparatus, including an insertion/removal unit for controlling insertion and removal of an auxiliary optical member on the optical path of the subjective measurer.

The tenth subjective optometry apparatus is the ninth subjective optometry apparatus, including a determiner for determining whether the auxiliary optical member is required or not based on an eye refractive power acquired by the objective measurer, wherein the insertion/removal unit controls insertion and removal of the auxiliary optical member on the optical path of the subjective measurer, based on a result of determination by the determiner.

The eleventh subjective optometry apparatus is the fifth subjective optometry apparatus including: a determiner for determining whether the auxiliary optical member is required or not based on the eye refractive power acquired by the objective measurer; and a display unit for displaying, on a monitor, notification information based on a result of determination by the determiner.

The twelfth subjective optometry apparatus is any one of the fifth to eleventh subjective optometry apparatus, wherein: the corrective optical system includes a right-left pair of an examinee's right-eye corrective optical system and an examinee's left-eye corrective optical system; and the optical member is shared by a right-eye optical path including the right-eye corrective optical system and a left-eye optical path including the left-eye corrective optical system.

The thirteenth subjective optometry apparatus includes: a subjective measurer including a light projecting optical system for projecting a target light flux toward an examinee's eye, and a corrective optical system disposed on an optical path of the light projecting optical system to change an optical characteristic of the target light flux, the subjective measurer subjectively measuring the optical characteristic of the examinee's eye, the subjective optometry apparatus further including an acquisitor for acquiring an eye refractive power of the examinee's eye that has been objectively measured, and a setter for setting an alignment allowable range for determining alignment state between the examinee's eye and the subjective measurer, based on the eye refractive power.

The fourteenth subjective optometry apparatus is the thirteenth subjective optometry apparatus, wherein the setter sets the alignment allowable range to become smaller as a diopter value increases in a plus direction or minus direction from zero diopter with reference to the zero diopter.

The fifteenth subjective optometry apparatus is the thirteenth or fourteenth subjective optometry apparatus, wherein: the corrective optical system includes a right-left pair of an examinee's right-eye corrective optical system and an examinee's left-eye corrective optical system, and is disposed on an optical path of the light projecting optical system to change an optical characteristic of the target light flux; and the subjective measurer includes an optical member shared by a right-eye optical path including the right-eye corrective optical system and a left-eye optical path including the left-eye corrective optical system, the optical member for guiding the target light flux corrected by the corrective optical system to the examinee's eye.

The sixteenth subjective optometry apparatus is any one of the thirteenth to fifteenth subjective optometry apparatus, including an objective measurer including a measurement optical system that emits measurement light toward the fundus of the examinee's eye and that receives reflected light thereof, the objective measurer objectively measuring the optical characteristic of the examinee's eye, wherein the acquisitor acquires the eye refractive power of the examinee's eye, based on a result of measurement by the objective measurer.

The first subjective optometry program is used in a subjective optometry apparatus including a subjective measurer including a light projecting optical system for projecting a target light flux toward an examinee's eye, and a corrective optical system disposed on an optical path of the light projecting optical system to change an optical characteristic of the target light flux, the subjective measurer subjectively measuring the optical characteristic of the examinee's eye, wherein the subjective optometry program, when executed by a processor of the subjective optometry apparatus, causes the subjective optometry apparatus to execute: an acquisition step of acquiring a refractive power of the examinee's eye; and a setting step of setting, based on the eye refractive power, an alignment allowable range for performing an alignment operation for the examinee's eye and the subjective measurer.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A subjective optometry apparatus comprising:

a subjective measurer including a light projecting optical system for projecting a target light flux toward an examinee's eye, a corrective optical system including a right-left pair of a right-eye corrective optical system and a left-eye corrective optical system and disposed on an optical path of the light projecting optical system to modify an optical characteristic of the target light flux, and an optical member shared by a right-eye optical path including the right-eye corrective optical system and a left-eye optical path including the left-eye corrective optical system, the optical member for guiding the target light flux corrected by the corrective optical system to the examinee's eye, the subjective measurer subjectively measuring an optical characteristic of the examinee's eye; and an objective measurer including a measurement optical system for emitting measurement light to a fundus of the examinee's eye and for receiving reflected light from the fundus, the objective measurer objectively measuring the optical characteristic of the examinee's eye via the optical member disposed on an optical path of the measurement optical system.

2. The subjective optometry apparatus according to claim 1, wherein an optical axis between the optical member and the examinee's eye in the subjective measurer, and an optical axis between the optical member and the examinee's eye in the objective measurer are coaxial.

3. The subjective optometry apparatus according to claim 1, wherein the optical member includes a concave mirror, and the subjective measurer guides the target light flux to the examinee's eye by reflecting, using the concave mirror, the target light flux corrected by the corrective optical system toward the examinee's eye, and guides an image of the target light flux corrected by the corrective optical system to the examinee's eye in such a way that a distance between a formation position of the image and the examinee's eye as sensed by the examinee becomes an optically predetermined examination distance.

4. The subjective optometry apparatus according to claim 1, further comprising:

a displacement detector for detecting displacement of an image of the corrective optical system with respect to the examinee's eye;

a right-left pair of deflecting members disposed between the corrective optical system and the examinee's eye;

a driver for driving the deflecting members; and a corrector for optically correcting a formation position of an image of the corrective optical system by deflecting an apparent light flux for guiding the image of the corrective optical system to the examinee's eye, by controlling the driver based on a result of detection by the displacement detector.

5. The subjective optometry apparatus according to claim 1, further comprising:

a correction setter for setting a correction amount for correcting optical aberration caused in the subjective measurer, based on a corrective power of the corrective optical system; and an aberration corrector for correcting the optical aberration caused in the subjective measurer based on the correction amount set by the correction setter.

6. The subjective optometry apparatus according to claim 5, wherein the aberration corrector corrects the optical aberration using the corrective optical system.

7. The subjective optometry apparatus according to claim 5, further comprising an insertion/removal unit for controlling insertion and removal of an auxiliary optical member on an optical path of the subjective measurer.

8. The subjective optometry apparatus according to claim 7, further comprising a determiner that determines whether the auxiliary optical member is required or not, based on an eye refractive power acquired by the objective measurer, wherein the insertion/removal unit controls insertion and removal of the auxiliary optical member on the optical path of the subjective measurer, based on a result of determination by the determiner.

9. The subjective optometry apparatus according to claim 5, further comprising:

a determiner for determining whether an auxiliary optical member is required or not based on an eye refractive power acquired by the objective measurer; and a display unit for displaying, on a monitor, notification information based on a result of determination by the determiner.

10. The subjective optometry apparatus according to claim 1, further comprising:

a controller for modifying a presentation distance of a target by the target light flux by modifying a formation position of an image of the target light flux;

a correction setter for setting a correction amount for correcting optical aberration caused in the subjective measurer, based on the presentation distance; and an aberration corrector for correcting the optical aberration caused in the subjective measurer based on the correction amount set by the correction setter.

11. The subjective optometry apparatus according to claim 1, further comprising:

a convergence angle modifier for modifying a convergence angle of the target light flux emitted from the right-eye optical path and the left-eye optical path;

a correction setter for setting a correction amount for correcting optical aberration caused in the subjective measurer, based on the convergence angle; and an aberration corrector for correcting the optical aberration caused in the subjective measurer based on the correction amount set by the correction setter.

12. The subjective optometry apparatus according to claim 1, further comprising:

an acquisitor for acquiring an objectively measured eye refractive power of the examinee's eye; and a setter for setting an alignment allowable range for determining an alignment state between the examinee's eye and the subjective measurer, based on the eye refractive power.

13. The subjective optometry apparatus according to claim 12, wherein the setter sets the alignment allowable range to be smaller as a diopter value increases in a plus direction or minus direction from zero diopter with reference to the zero diopter.

14. The subjective optometry apparatus according to claim 12, wherein the acquisitor acquires the eye refractive power of examinee's eye based on a result of measurement by the objective measurer.

* * * * *